US011998252B2

(12) United States Patent
Weiner et al.

(10) Patent No.: US 11,998,252 B2
(45) Date of Patent: Jun. 4, 2024

(54) SYSTEM AND METHOD FOR BONE FIXATION

(71) Applicant: Nextremity Solutions, Inc., Warsaw, IN (US)

(72) Inventors: Lon S. Weiner, Warsaw, IN (US); Stuart D. Katchis, Warsaw, IN (US); John R. Pepper, Warsaw, IN (US); Ryan Schlotterback, Warsaw, IN (US); Greg Denham, Warsaw, IN (US)

(73) Assignee: MEDARTIS AG, Basel (CH)

( * ) Notice: Subject to any disclaimer, the term of this patent is extended or adjusted under 35 U.S.C. 154(b) by 109 days.

(21) Appl. No.: 17/455,049

(22) Filed: Nov. 16, 2021

(65) Prior Publication Data
US 2022/0151666 A1    May 19, 2022

Related U.S. Application Data

(60) Provisional application No. 63/244,310, filed on Sep. 15, 2021, provisional application No. 63/185,761, filed on May 7, 2021, provisional application No. 63/115,460, filed on Nov. 18, 2020.

(51) Int. Cl.
*A61B 17/80* (2006.01)
*A61B 17/84* (2006.01)

(52) U.S. Cl.
CPC ...... *A61B 17/8061* (2013.01); *A61B 17/8014* (2013.01); *A61B 17/809* (2013.01); *A61B 17/842* (2013.01)

(58) Field of Classification Search
CPC ............ A61B 17/8061; A61B 17/8014; A61B 17/809; A61B 17/842
See application file for complete search history.

(56) References Cited

U.S. PATENT DOCUMENTS

| | | | |
|---|---|---|---|
| 5,190,545 | A | 3/1993 | Corsi et al. |
| 5,665,089 | A | 9/1997 | Dall et al. |
| 5,902,305 | A | 5/1999 | Beger et al. |
| 5,993,452 | A | 11/1999 | Vandewalle |
| 6,761,720 | B1 | 7/2004 | Senegas |
| 7,229,444 | B2 | 6/2007 | Boyd |
| 7,731,718 | B2 | 6/2010 | Schwammberger et al. |

(Continued)

FOREIGN PATENT DOCUMENTS

| | | |
|---|---|---|
| CN | 204484284 U | 7/2015 |
| CN | 109223152 A | 1/2019 |

(Continued)

OTHER PUBLICATIONS

Japanese Patent Application No. 2021-105275 First Office Action dated Oct. 20, 2023, 6 pp.

(Continued)

*Primary Examiner* — Sameh R Boles
(74) *Attorney, Agent, or Firm* — Heslin Rothenberg Farley & Mesiti P.C.; Brett M. Hutton, Esq.

(57) ABSTRACT

A system for fixating a bone includes a buckle having a plurality of lock bars and a hook. A cord may connect the hook with an opposite end of the buckle and around a bone. The buckle may include lock bars on the opposite end of the buckle to receive the cord and allow a frictional resistance to a loosening of the cord around the bone to facilitate a reduction of a fracture of the bone.

14 Claims, 51 Drawing Sheets

(56) References Cited

U.S. PATENT DOCUMENTS

| | | |
|---|---|---|
| 8,685,025 B2 | 4/2014 | Anapliotis |
| 8,764,809 B2 | 7/2014 | Lorenz et al. |
| 9,138,245 B2 | 9/2015 | Mebarak |
| 9,693,812 B2 | 7/2017 | Zeetser et al. |
| 10,966,764 B2 | 4/2021 | McCormick |
| 2005/0288711 A1* | 12/2005 | Fallin ................. A61B 17/0401 606/232 |
| 2008/0234679 A1 | 9/2008 | Sarin et al. |
| 2014/0018807 A1 | 1/2014 | Foerster et al. |
| 2017/0181780 A1 | 6/2017 | Cremer et al. |
| 2018/0161083 A1 | 6/2018 | Kobayashi |
| 2019/0099206 A1 | 4/2019 | Senegas |
| 2019/0133653 A1 | 5/2019 | Swarts |

FOREIGN PATENT DOCUMENTS

| | | |
|---|---|---|
| CN | 209595876 U | 11/2019 |
| DE | 20203174 U1 | 7/2002 |
| GB | 2257913 A | 1/1993 |
| GB | 2598454 A | 2/2022 |
| JP | H07506988 A | 8/1995 |
| JP | 2005137757 A | 6/2005 |
| JP | 2018509276 A | 4/2018 |
| KR | 20160058515 A | 5/2016 |
| WO | 9318716 | 9/1993 |
| WO | 9318716 A1 | 9/1993 |
| WO | 2006135935 A1 | 12/2006 |

OTHER PUBLICATIONS

"Locking Plate Fixation of Periprosthetic Femur Fractures with and without Cerclage Wires", N.A. Ebraheim, MD, 2013 Chinese Orthopaedic Association and Wiley Publishing Asia Pty Ltd, pp. 183-187.

"Vascular complication after percutaneous femoral cerclage wire" M. Ehlinger, Orthopaedics & Traumatology: Surgery & Research 104 (2018), pp. 377-381.

UK Search Report dated Dec. 8, 2020.

UKIPO Search Report dated Dec. 23, 2021.

United Kingdom Search Intellectual Property Search Report dated Mar. 9, 2022.

* cited by examiner

SYSTEM AND METHOD FOR BONE FIXATION

CROSS-REFERENCE TO RELATED APPLICATIONS

The present application claims priority to U.S. Provisional Application No. 63/115,460 filed Nov. 18, 2020, U.S. Provisional Application No. 63/185,761 filed May 7, 2021, and U.S. Provisional Application No. 63/244,310 filed on Sep. 15, 2021, which are incorporated herein by reference in its entirety.

The present application is related to U.S. application Ser. No. 16/910,328 filed Jun. 24, 2020, which claims the benefit of U.S. Provisional Application Ser. No. 62/865,676 filed Jun. 24, 2019, and U.S. Provisional Application No. 62/905,017 filed Sep. 24, 2019, and to U.S. application Ser. No. 17/358,706 filed on Jun. 25, 2021, which claims the benefit of U.S. Provisional Application Ser. No. 63/043,841 filed on Jun. 25, 2020, U.S. Provisional Application No. 63/185,761 filed May 7, 2021, U.S. Provisional Application No. 63/244,310 filed on Sep. 15, 2021, which are incorporated herein by reference in their entireties.

FIELD OF THE INVENTION

This application relates generally to apparatuses, devices, and methods for bone fixation and more particularly to apparatuses, devices, and methods for cerclage related to skeletal fracture fixation and instrumentation to facilitate fracture reduction.

BACKGROUND

Femoral fractures may occur naturally or iatrogenically during total hip arthroplasty. Depending on the fracture pattern, cerclage alone, cerclage with a plate or plates, cerclage with a strut, cerclage with an extended hip stem, or cerclage with a combination of plates, struts, and/or extended hip stems may be used for bone fixation. However, a problem with cerclage is that it may create poor bone unions without using additional support devices. In particular with total hip arthroplasty using additional support may not be desirable or possible. With femoral fractures, there may be a high load on the cerclage wires resulting in adjacent boney erosion and loss of fixation due to wire migration.

Fracture reduction of long bones often involves realigning spiral fractures and multiple pieces. Bone clamps are often hinged devices (e.g., pliers) with specialized tips or spurs to grab (e.g., engage and hold) bone. The closing of such a clamp puts force on the fragments and pushes them closer together. Limits of traditional clamps are they produce forces linearly, or very close to linearly. Such clamps may also be bulky when multiple clamps are used, as is common, access to a fracture site for placement of hardware (e.g., plates or screws) may be is restricted. Also, single plane forces produced by a clamp cannot adequately reduce some fractures. Further, clamps must be removed after fixation, and sometime loss of reduction and malalignment may occur due to such removal.

In another example, solid cerclage wire has been used to provide circumferential forces to reduce fractures. Use of such wire has some drawbacks, including the wire may be so stiff that manipulating the wire may be very difficult. Also, if the wire is not initially placed ideally, reforming the wire to fit in another location is nearly impossible. Further, the traditional method of tensioning solid cerclage wire involves twisting the ends in a tight spiral. This required specialized bulky tools, and the resulting twisted wire may be extremely stiff and often cannot be flattened to either work around. If the twisted wire is left in place, the wire may irritate soft tissues. These limitations have seen the use of solid temporary wire fixation drop to such that this method is rarely used.

There is a need for a device that provides improved bone unions while minimizing boney erosion and loss of fixation due to wire migration.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

DETAILED DESCRIPTION OF THE EMBODIMENTS

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention. Thus, all the implementations described below are exemplary implementations provided to enable persons skilled in the art to make or use the embodiments of the disclosure and are not intended to limit the scope of the disclosure, which is defined by the claims.

The following description references systems, methods, and apparatuses for use in femoral fixation. However, those possessing an ordinary level of skill in the relevant art will appreciate that fixation of other bones are suitable for use with the foregoing systems, methods and apparatuses. Likewise, the various figures, steps, procedures and work-flows are presented only as an example and in no way limit the systems, methods or apparatuses described to performing their respective tasks or outcomes in different time-frames or orders. The teachings of the present invention may be applied to fixation related to any bone.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
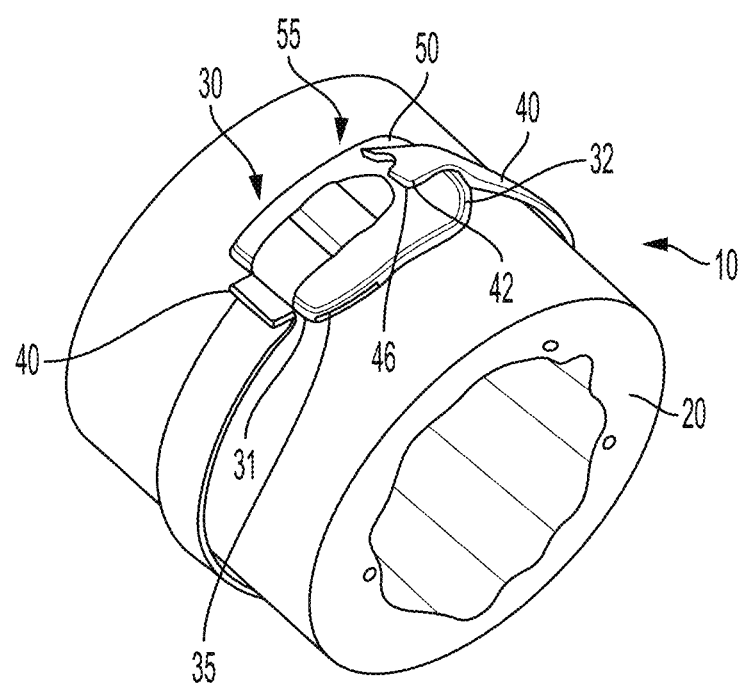
FIG. 1 is a perspective view of a system for fixing bone including a buckle and cord in accordance with the present invention.

A system 10 for fixating or reducing a bone 20 may include a connector or buckle 30 connected to a strap, belt or cord 40 extending around bone 20, as depicted in FIG. 1.

Figure 2:
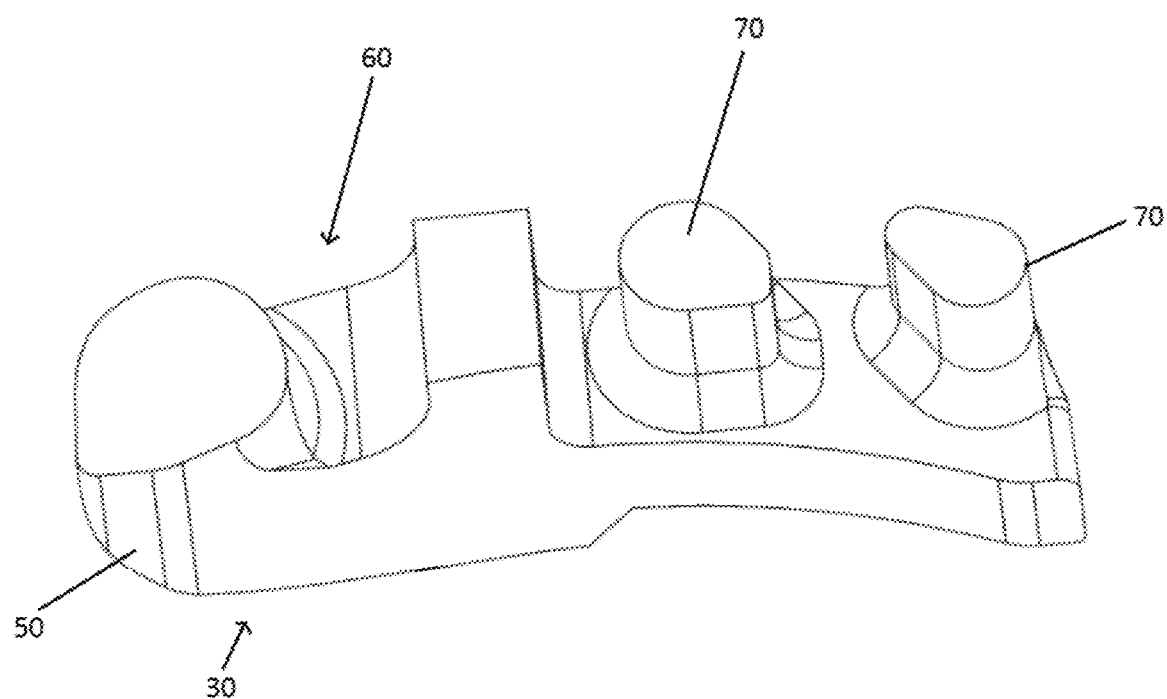
FIG. 2 is a cross-sectional view of a portion of the buckle of FIG. 1 including locking bars.
Figure 3:
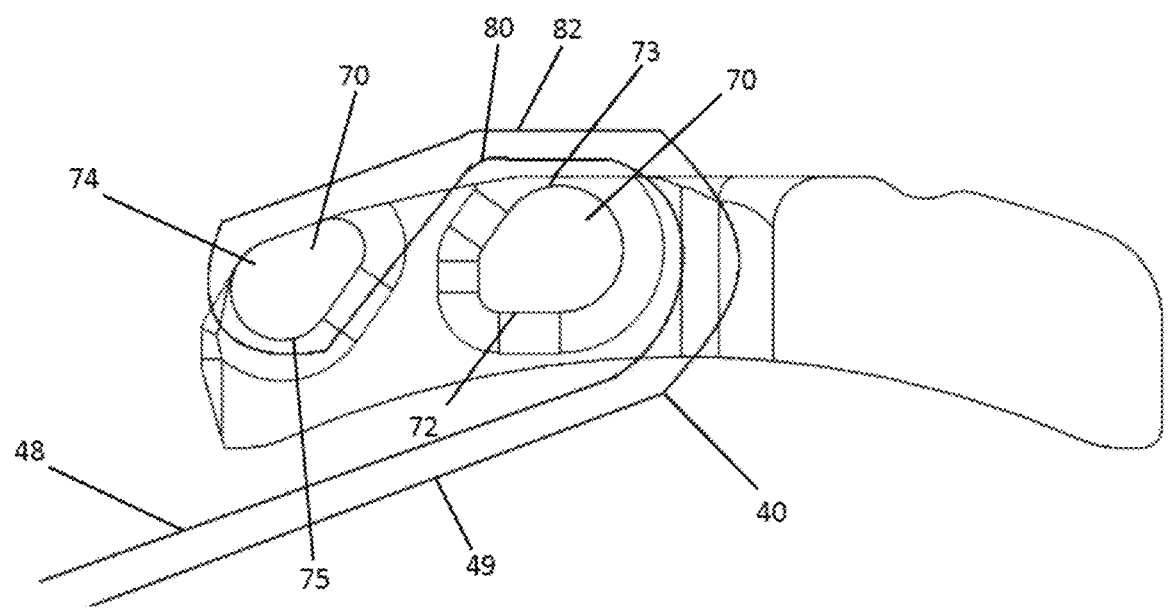
FIG. 3 is a side cross-sectional view of the buckle of FIG. 1 including locking bars and showing a path of the cord of FIG. 1 around the locking bars.
Figure 4:
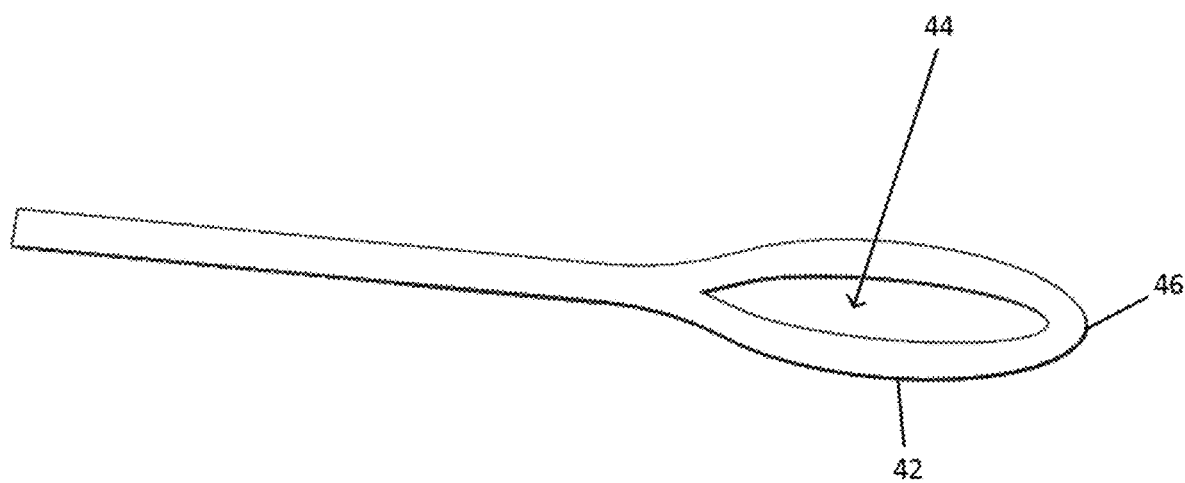
FIG. 4 is a side view of a distal end of the cord of FIG. 1 including a loop for attaching to the buckle.

Buckle 30 may include a plurality of lock bars 70 and a hook 50 as depicted cross-sectionally in FIGS. 2-3. Lock bars may have a cross-sectional tear drop shape as depicted in the figures or could have a cross-sectional rounded shape. Hook 50 may be located at a distal end of buckle 30 and may have an opening 55 to allow a cord (e.g., cord 40) to pass therethrough into a receiving cavity 60. Cord 40 may have a loop 42 connectable to a distal portion 32 of buckle 30 when an opening 44 of loop 42 receives distal portion therein. When connected to buckle 30, a distal end 46 of cord 40 may be received in cavity 60. Cord 40 may also be connected to buckle 30 in other ways besides a loop, such as a knot, a ferrule, a non-eye splice, hitch or embedded internal stopper.

Buckle 30 could be made of stainless steel, surgical grade plastic, Titanium, PEEK, or Cobalt Chrome, for example. Also, cord 40 may be made of a material that may be left in a body for a period of time to allow a bone to heal, such as an Ultra-High Molecular Weight Polyethylene (UHMWPE), for example. Cord 40 may be a 50 cm tape with a width of 3.5 mm and a thickness of 0.6 mm, for example. Further cord 40 may be flexible (e.g., a suture tape) and may be made from strands, or braided stranded, of fine wires of metal or metallic alloy, such as cobalt chrome, stainless steel, titanium and titanium alloys.

A proximal end 48 of cord 40 may be connected to a proximal end 31 of buckle 30. For example, cord 40 may be connected to lock bars 70 as depicted in FIGS. 2-3. After extending around bone 20 as depicted in FIG. 1, cord 40 may extend distally toward hook 50 under lock bars 70 and extend upwardly away from bone 20, before reversing course and turning proximally away from hook 50 around a distal bar 72 of locking bars 70. Cord 40 may extend from distal bar 72 proximally away from hook 50 and then downwardly toward bone 20 before extending distally such that cord 40 goes around a proximal bar 74 of lock bars 70. From a bottom side 75 of proximal bar 74, cord 40 may extend upwardly and distally toward a top side 73 of distal bar 72. Cord 40 may extend upwardly over and/or contact top side 73 with a first cord portion 80 thereof while a second cord portion 82 may contact an opposite side of first cord portion 80 relative to top side 73. Cord 40 may extend from top side 73 distally toward hook 50 then downwardly toward bone 20 while contacting bar 72. First cord portion 80 and second cord portion may contact each other as cord 40 extends proximally from bar 72 away from hook 50. Proximal end 48 of cord 40 may be located on top of a distally extending portion 49 extending away from locking bars 70 around bone 20 toward hook 20. Proximal end 48 may be pulled by a user in a direction opposite from hook 50 to pull cord 40 through and past locking bars 70 as described above. A path of cord 40 past and against bars 70 may provide a frictional resistance to a release of cord 40 from bars 70 such that cord 40 may be tightened and such position retained to hold fractured portions of bone 20 for a period of time, or may remain in place, to allow a reduction of a fracture.

As described, system 10 may be utilized for fixating or reducing bone 20 and a process for such fixating or reducing is described as follows.

Figure 5:
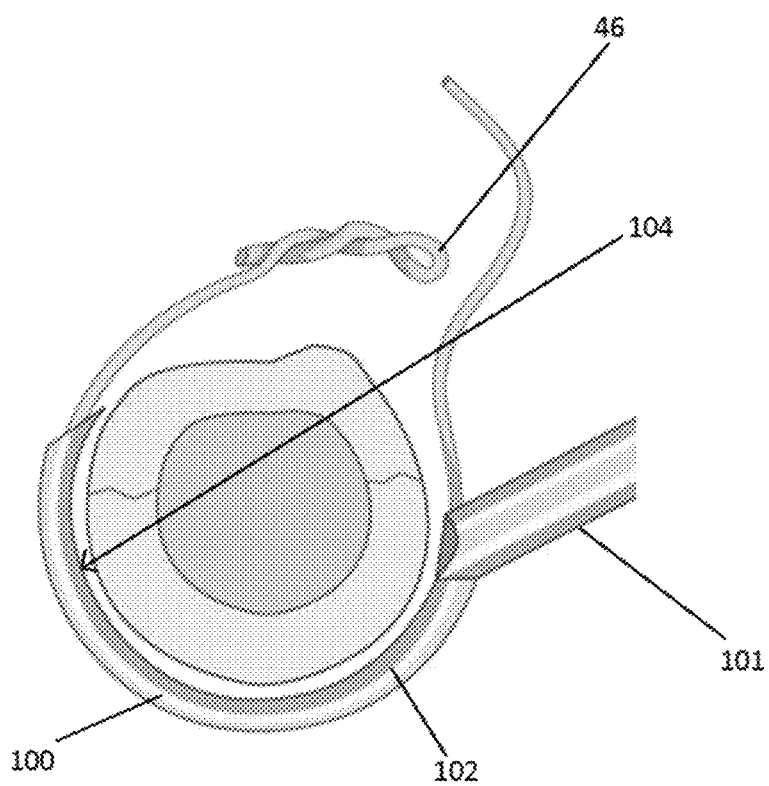
FIG. 5 is a side view of a passer including the cord of FIG. 1 received in a cavity therein.
Figure 6:
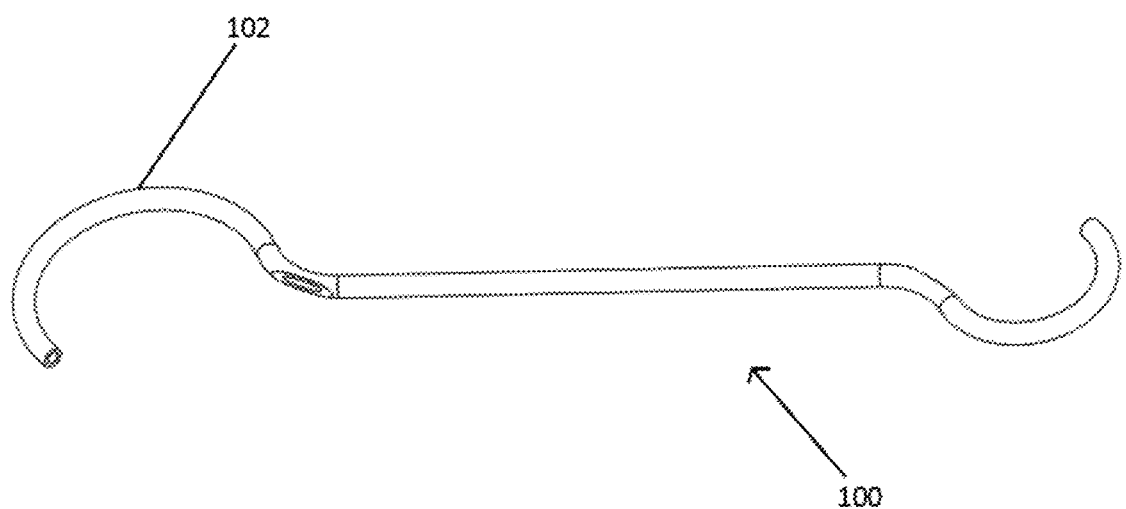
FIG. 6 is a side view of the passer of FIG. 5.

Cord 40 may be passed around bone 20 and under tissue and muscle 11 using a passer 100 as depicted in FIGS. 5-6. Passer 100 may have a curved extension portion 102 having a cavity 104 along an inner circumferential side for receiving cord 40 prior to a procedure such that passer 100 holding cord 40 in cavity 104 may be manipulated around bone 20 and under tissue and muscle 11, such that distal end 46 may be passed to an opposite side of bone 20 relative to a handle portion 101 of passer 100. Passer 100 may be removed from bone 20 with cord 40 remaining around bone 20 such that distal end 46 and proximal end 48 may be located on a same side of bone 20.

Figure 7:
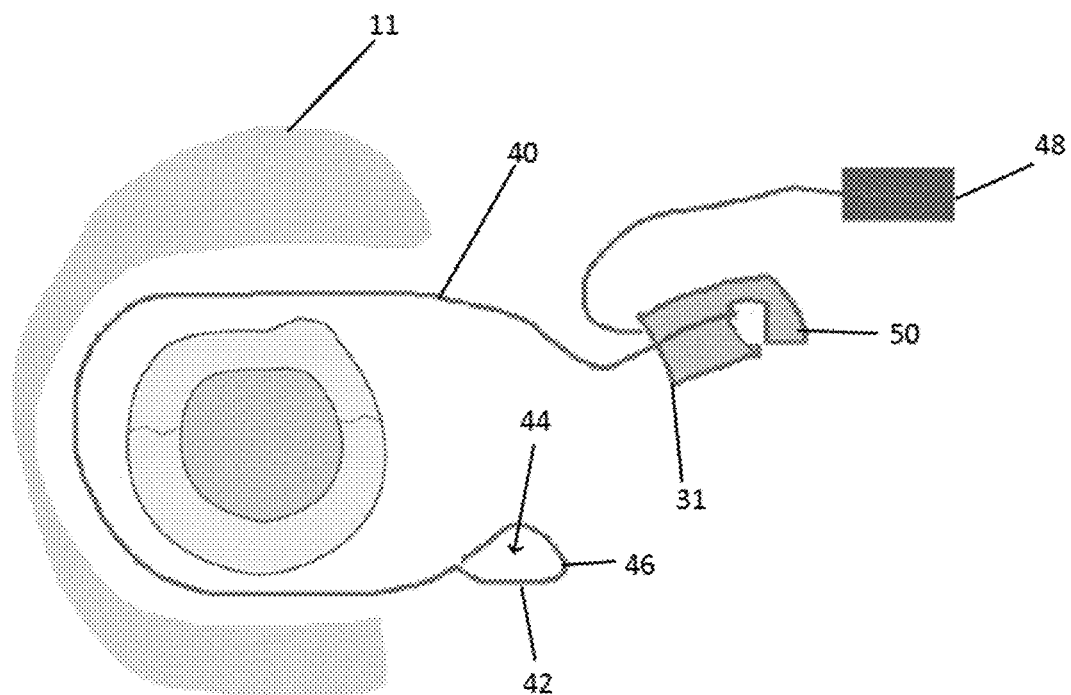
FIG. 7 is a side view of the system of FIG. 5 including the cord attached to a proximal end of the buckle and a loop of the cord configured to be attached to the buckle.
Figure 8:
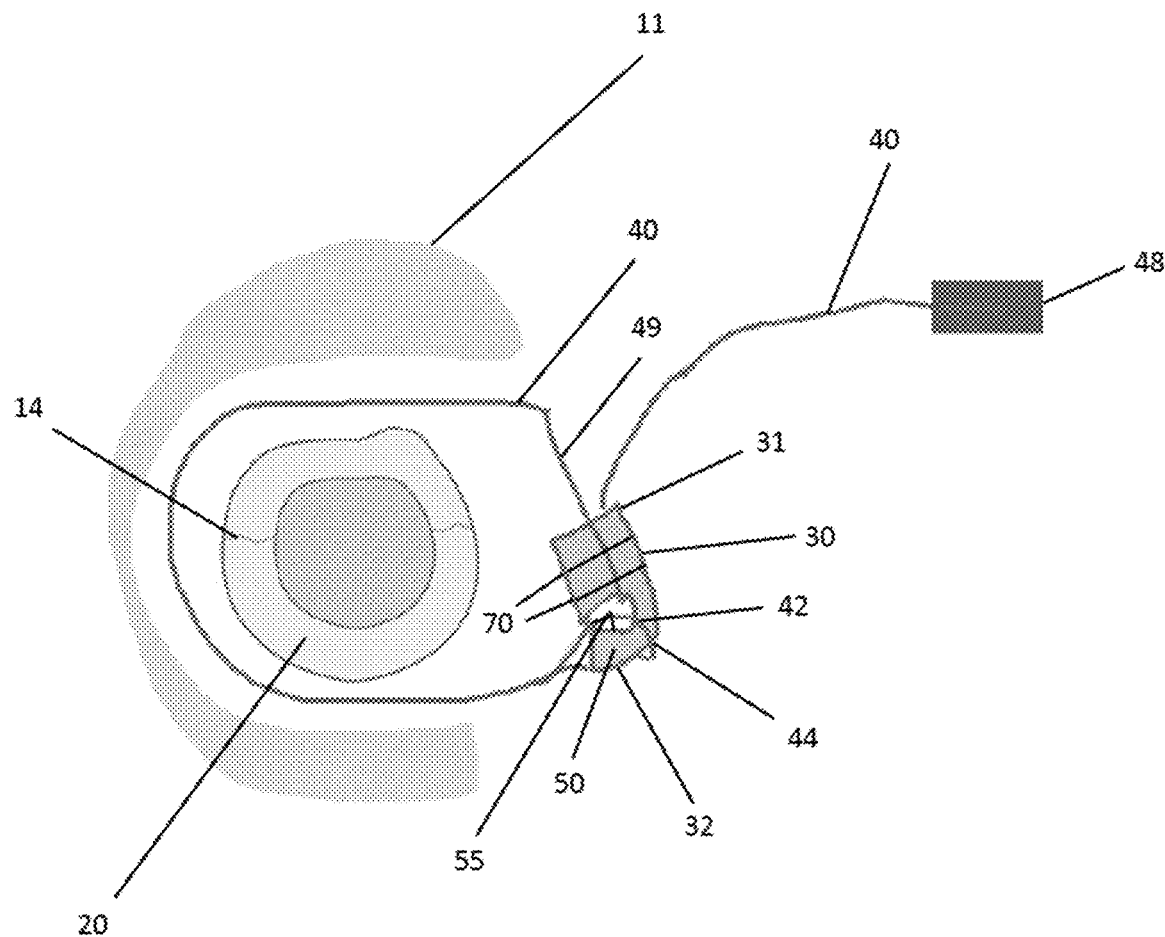
FIG. 8 is a side view of the system of FIG. 7 with the buckle and loop attached to each other.
Figure 9:
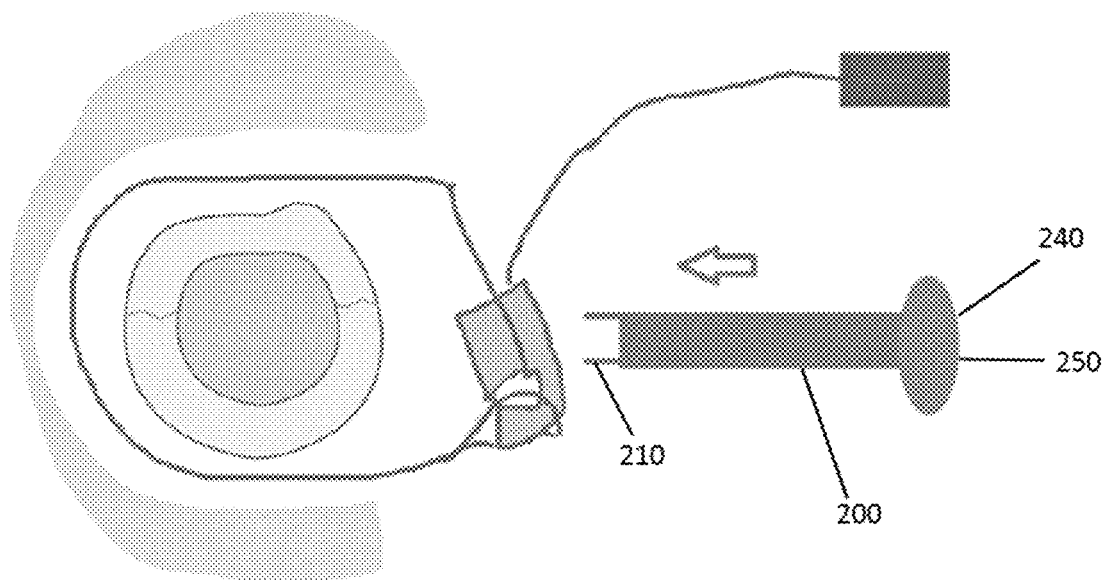
FIG. 9 is a side view of the system of FIG. 8 further including a tensioner.
Figure 10:
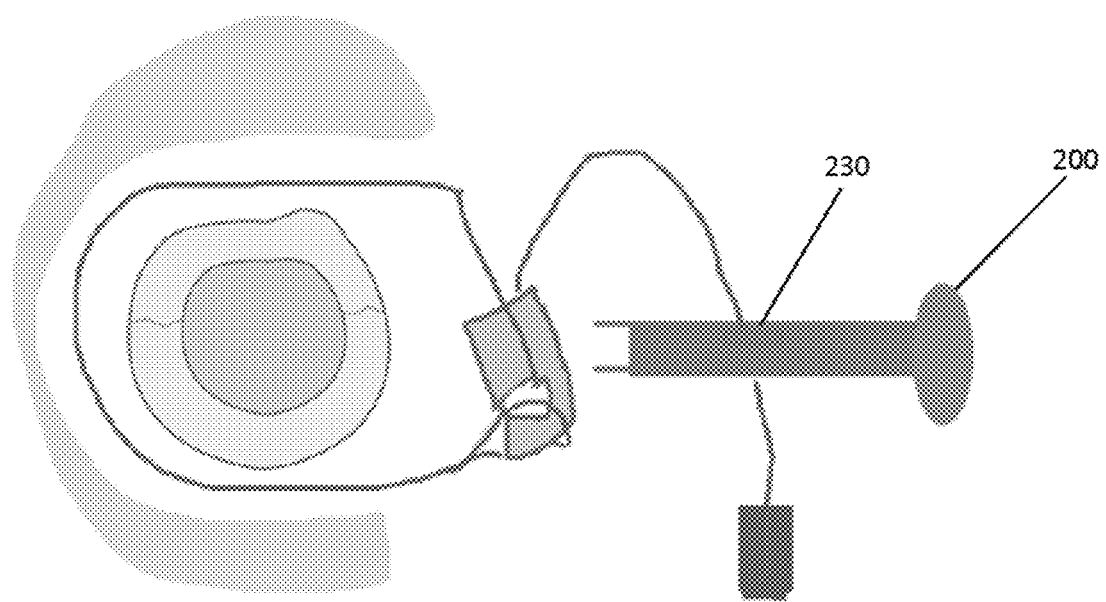
FIG. 10 is a side view of the system of FIG. 9 with the proximal end of the cord received through a passage of the tensioner.
Figure 11:
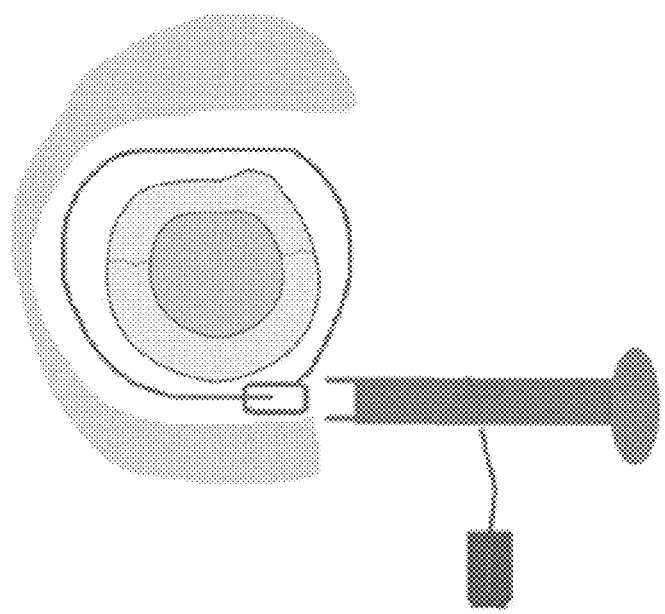
FIG. 11 is a side view of the system of FIG. 10 with the tensioner aligned to connect to the buckle.

As depicted schematically in FIGS. 7-9, loop 44 of cord 40 may be connected to hook 50 and received in cavity 55. Cord 40 may be threaded around and connected to lock bars 70 as described above, depicted in FIGS. 1-3, and depicted schematically in FIGS. 7-9. A user may tighten cord 40 around bone 20 to reduce a fracture 14 of bone 20 by holding buckle 30 while pulling proximal end 48.

Figure 14:
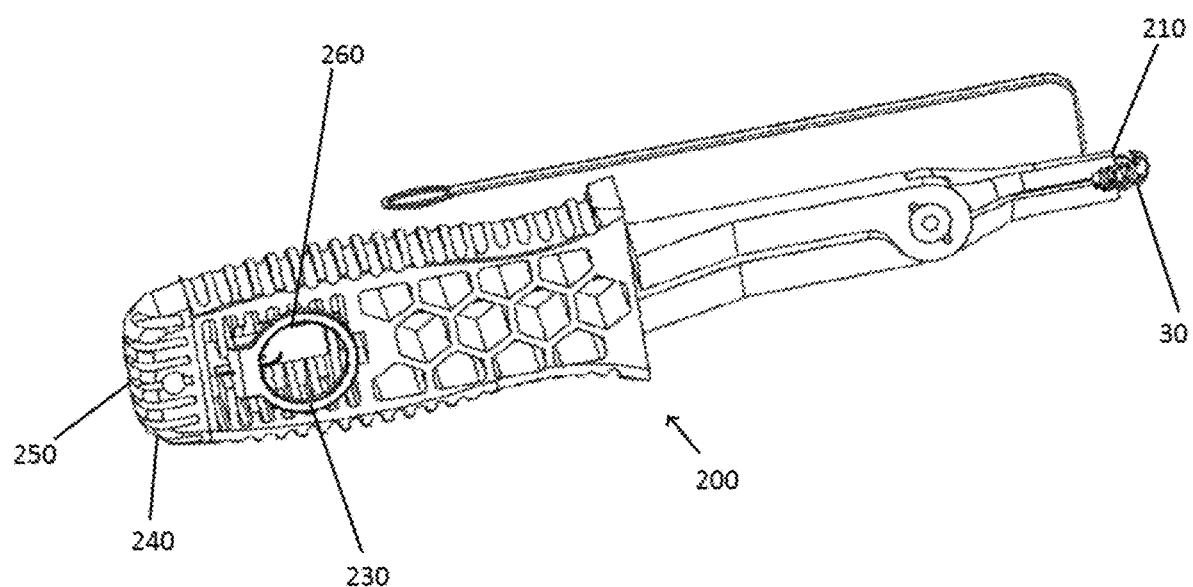
FIG. 14 is a perspective view of the tensioner of FIG. 13.

In an example, buckle 30 may include a pair of slots 35 located on opposite axial sides of buckle 30 relative to bone 20 as depicted in FIG. 1. Slots 35 may be configured (e.g., shaped and dimensioned) to receive arms 210 of a tensioner 200 depicted in FIG. 14 and depicted schematically in FIGS. 9-13. After cord 40 is passed around bone 20 and connected to buckle 30, proximal end 48 of cord 40 may be passed through a receiving passage 230 in tensioner 200 to allow cord 40 to be drawn or pulled by tensioner 200. Arms 210 may be received in slots 35 to connect tensioner 200 to buckle 30.

Figure 12:
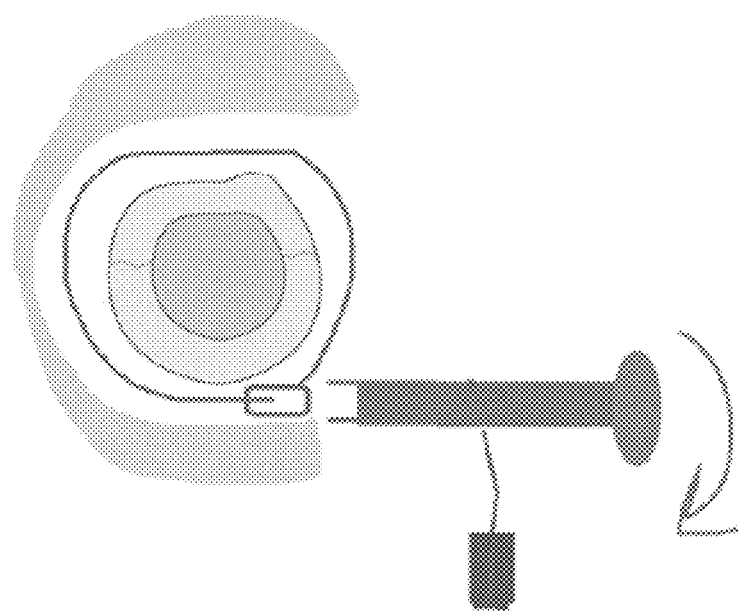
FIG. 12 is a side view of the system of FIG. 11 showing the direction of rotation of a handle of the tensioner to draw the cord to tighten the cord relative to the buckle and the bone.
Figure 13:
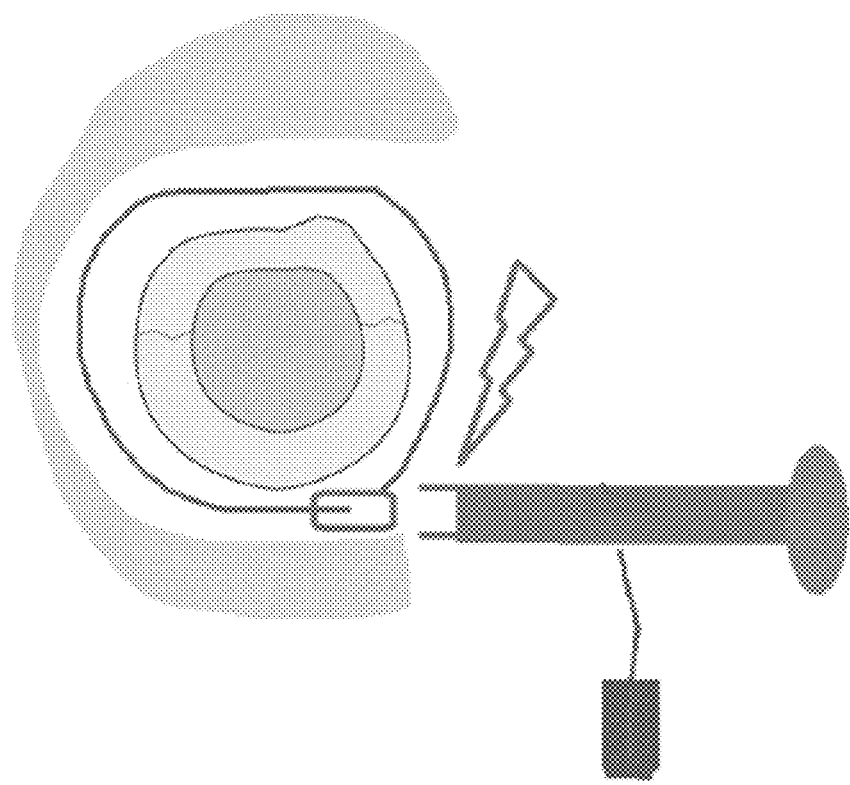
FIG. 13 is a side view of the system of FIG. 11 showing the cord being cut.

A handle 240 of tensioner 200 may be rotated by a user to cause the drawing of cord 40 by tensioner 200 away from bone 20 and toward a proximal end 250 of tensioner 200 as depicted in FIG. 12. A force provided on cord 40 by the drawing by tensioner 200 may pull cord 40 around lock rods 70 of buckle 30 to tighten cord 40 around bone 20, as described above, such that cord 40 is held at a particular tightness by friction provided by the path of cord 40 around lock bars 70 to allow a reduction of fracture 14, for example.

Tensioner 200 may include a rod 260 connected to handle 240 and including passage 230 to provide the drawing of cord 40 as described.

After cord 40 is tightened a desired amount around bone 20, e.g., when fracture 14 is placed in a desired position as determined by a user or surgeon, cord 40 may be cut such that proximal end 48 is at or adjacent to proximal end 31 of buckle 30 such as depicted in FIG. 1. Any sutures in the area around the fracture may be closed with buckle 30 and cord 40 remaining.

As indicated, buckle 30 and cord 40 may be utilized to for temporary fixation of a bone (e.g., fracture 14 of bone 20) with the buckle and cord being removed after a period of time (e.g., after the bone has healed) or buckle 30 and cord 40 may remain in vivo after the bone has healed. In an example, a bone plates may be placed over a tape (e.g., cord 40), to allow such a plate to be attached to appropriate portions of a bone (e.g., bone 20) cord 20 and buckle 30 are in place to reduce a fracture (e.g., fracture 14) Cord 40 may be cut and removed if the plate is adequate to hold the bone and cord 40 is not also needed. Such plates may also be applied to a bone other than over a cord to hold such bone to reduce a fracture, for example. Such plates or other surgical hardware may also remain in vivo with or without such a buckle and cord (e.g., buckle 30 and cord 40) hardware to stabilize a bone (e.g., a fracture 14) during a consolidation thereof.

In an example, multiple instances of a buckle and cord (e.g., buckle 30 and cord 40) may be utilized to fixate a fracture (e.g., fracture 14) or otherwise to hold a bone (e.g., bone 20) together at various longitudinal points along such a bone. A fracture may thus be segmentally reduced by incrementally drawing fragments of bone (e.g., bone 20) together. Such fracture reduction may be a dynamic operation and forces may need to be redirected due to an often-complex geometry of mating faces that may be adjusted and moved back together by manipulating a series of buckles and cord (e.g., multiple instances of buckle 30 and cord 40).

In another example not depicted, a holding member (not shown) may be used in place of tensioner 200 with the holding member including arms configured as arms 210 described above for tensioner 200, but not including a mechanism for drawing cord 40. Instead the holding member may include a holding portion extending away from the arms to allow a user to hold the holding member thereby holding buckle 30 via the arms. While holding the holding member to hold the buckle a user may pull proximal end 48 of cord 40 to secure cord 40 around bone 20 to reduce fracture 14, for example.

Figure 15:
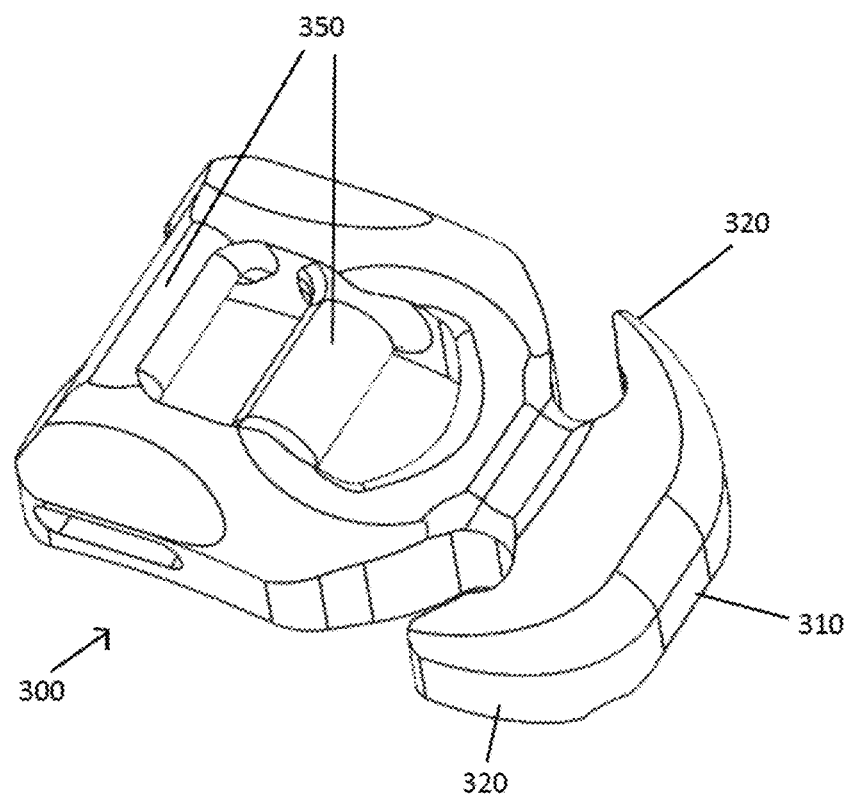
FIG. 15 is a perspective view of another example of a buckle useful in place of the buckle of FIG. 1.
Figure 16:
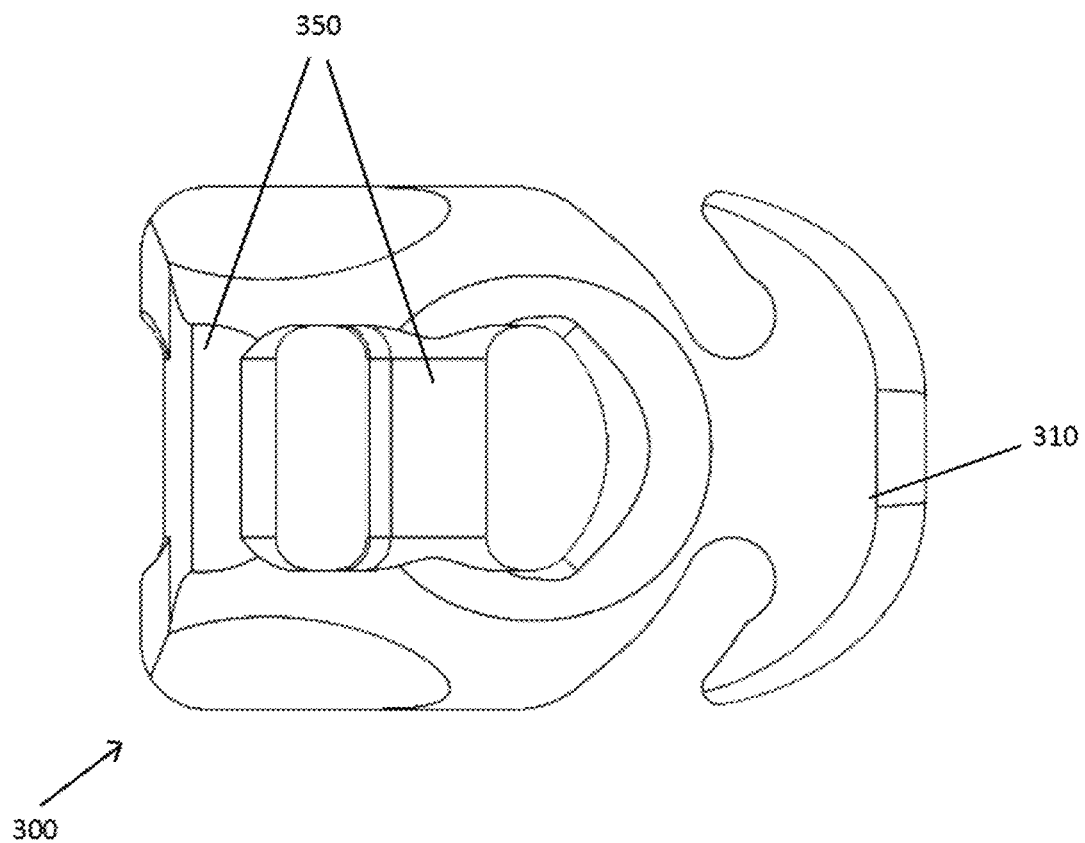
FIG. 16 is a top view of the buckle of FIG. 15.

In another example depicted in FIGS. 15-16, a buckle 300 may be utilized in place of buckle 30 described above and may include a hook 310 having two outwardly facing prongs 320 configured to be attached to loop 44 of cord 40. Lock bars 350 may be utilized to connect to cord 40 as described above for lock bars 70.

Figure 17:
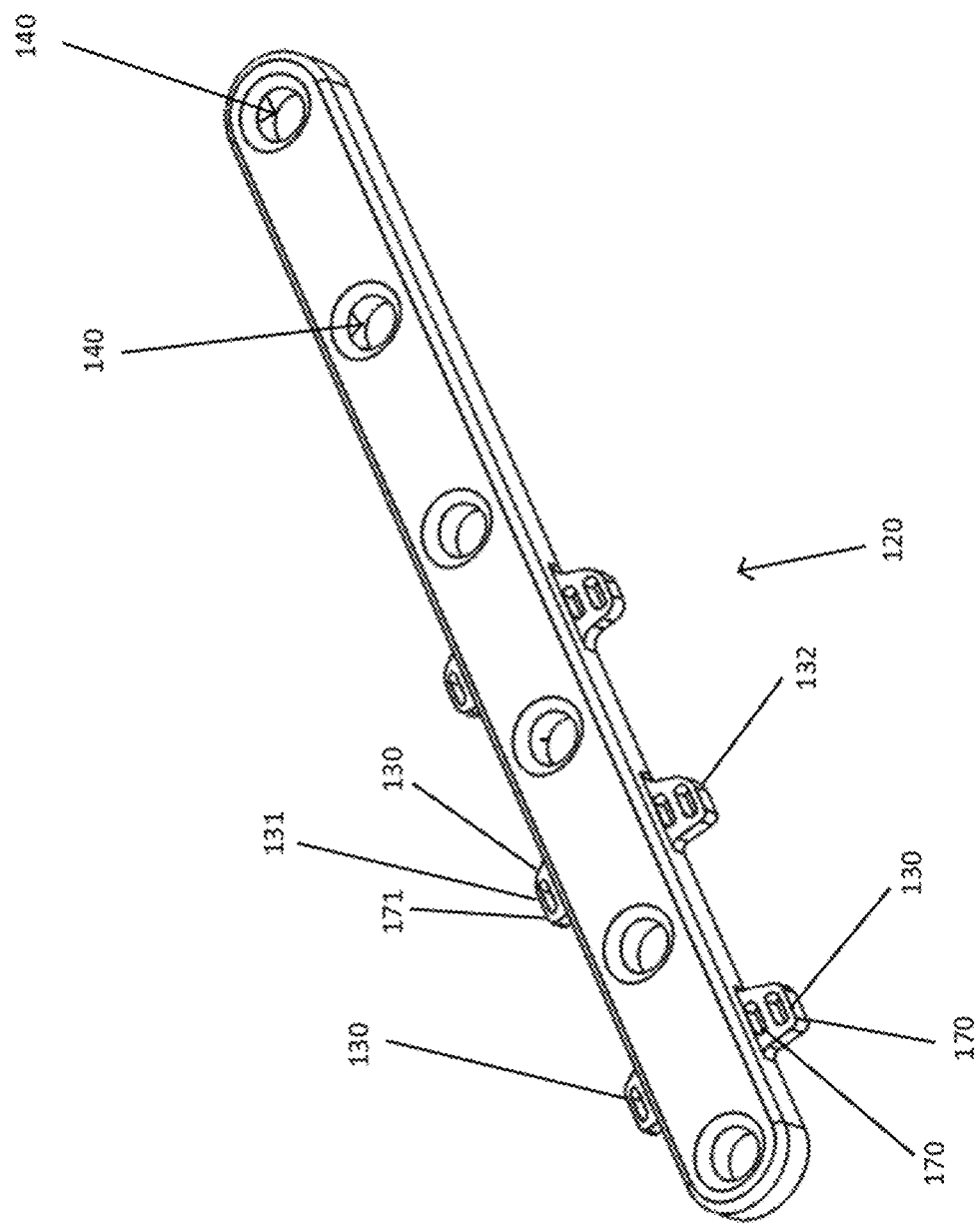
FIG. 17 is a perspective view of a plate having a plurality of buckles in accordance with the present invention.
Figure 18:
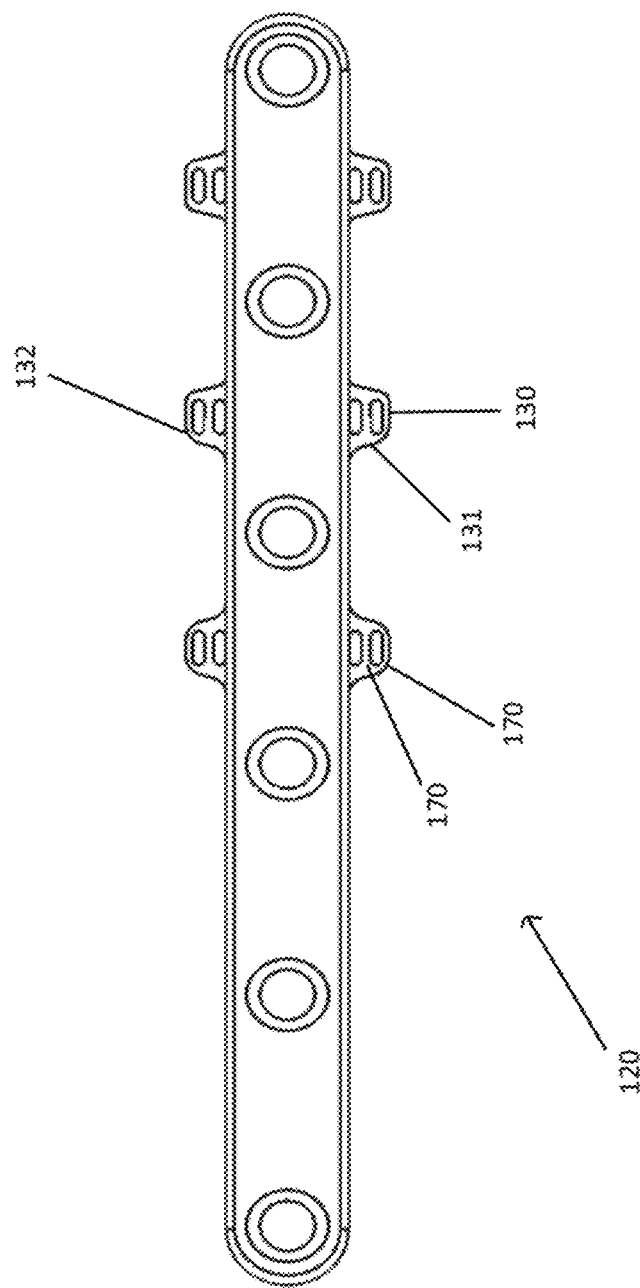
FIG. 18 is a top view of the plate of FIG. 17.

In an example depicted in FIGS. 17-18, a plate 120 may include buckles 130 having lock bars 170 and a plurality of openings 140 for receiving screws therethrough to allow plate 120 to be fastened to a bone (e.g., bone 20). A cord (e.g., cord 40) may be attached to a first buckle 131 and a second buckle 132 of buckles 130 as described above for cord 40 being attached to buckle 30. In an undepicted example, second buckle 132 may be replaced by a hook, similar to hook 50 described above, and a cord (e.g., cord 40) may be attached to lock bars 171 of buckle 131 and the hook as described for lock bars 70, hook 50 and cord 40. Buckles. Multiple instances of such buckles may be present along a length of a plate (e.g., plate 120). Each instance of a cord (e.g., cord 40) attached to opposing buckles (e.g., first buckle 131 and second buckle 132) may be tensioned at a same or differing amount around a bone (e.g., bone 20) to achieve a particular therapeutic purpose for reducing a fracture (e.g., fracture 14) Screws may be inserted though openings 140 after one or more such cords are attached to one or more of buckles 130 along plate 120 to secure and reduce a fracture in a bone (e.g., bone 20).

Figure 19:
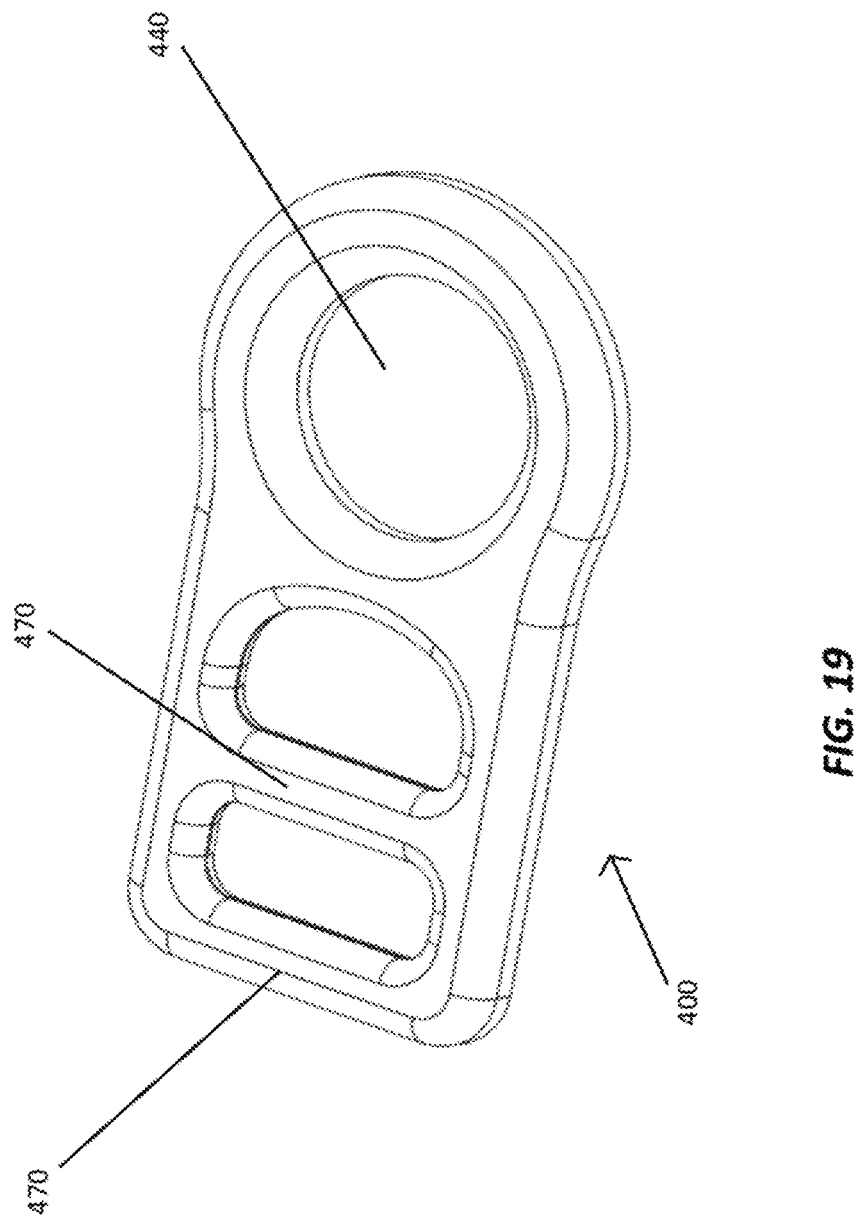
FIG. 19 is a perspective view of a washer having a plurality of lock bars in accordance with the present invention.
Figure 20:
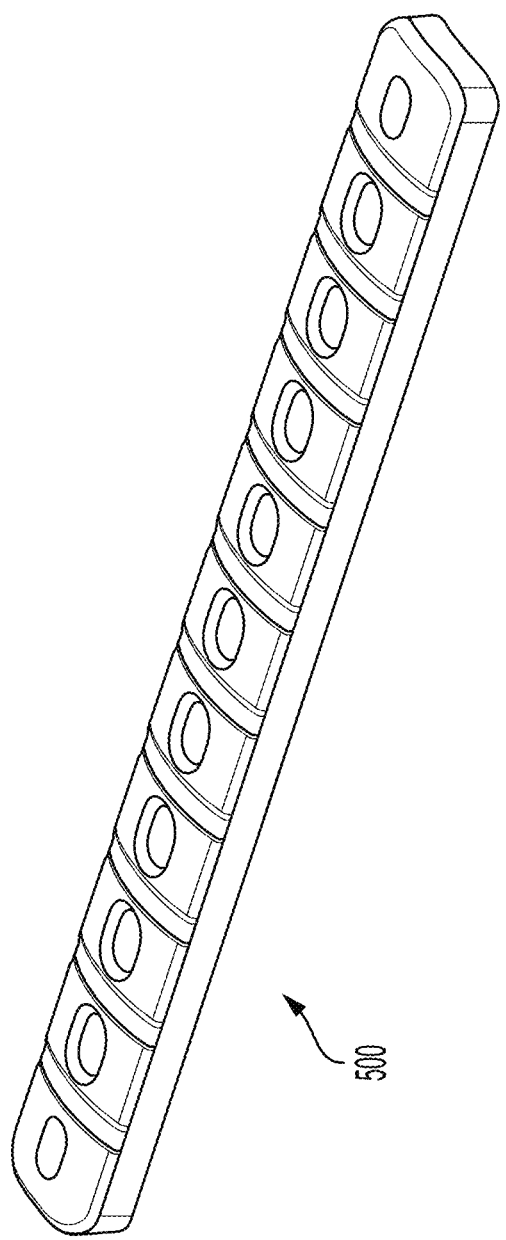
FIG. 20 is a perspective view of a plate for use in fixating a bone in accordance with the present invention.
Figure 21:
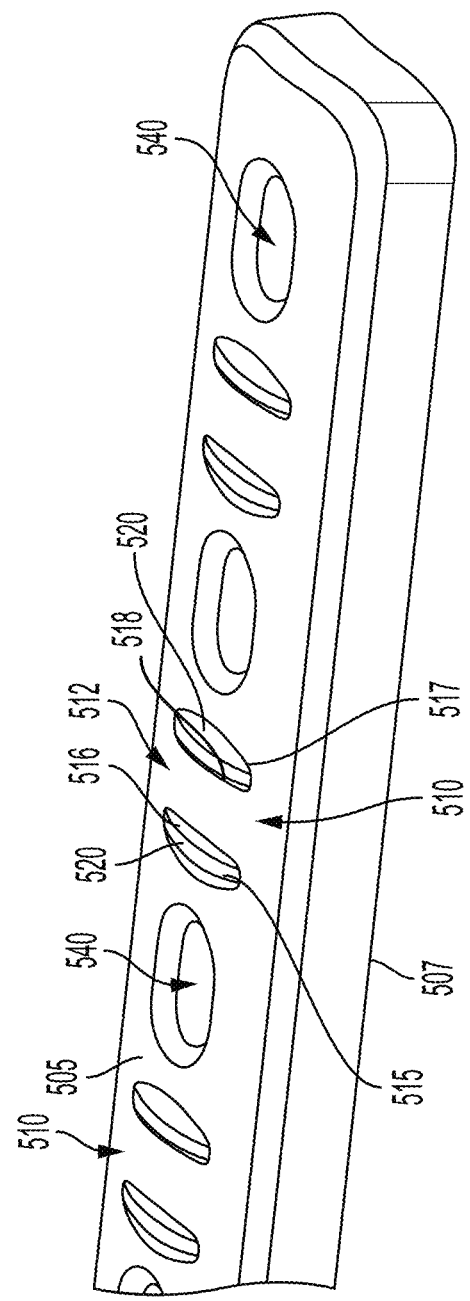
FIG. 21 is a close-up view of the plate of FIG. 20.
Figure 22:
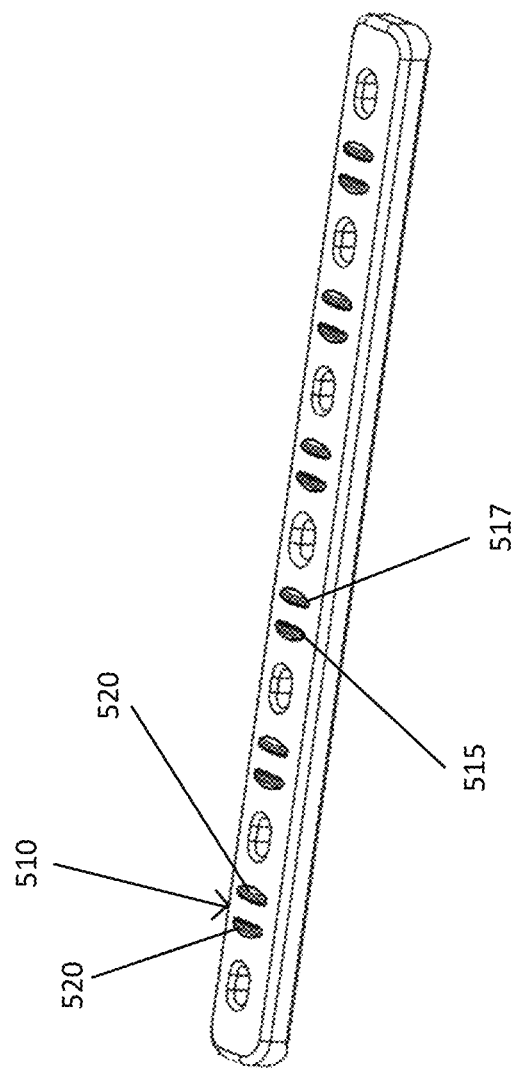
FIG. 22 is a perspective view of the plate of FIG. 20.
Figure 23:
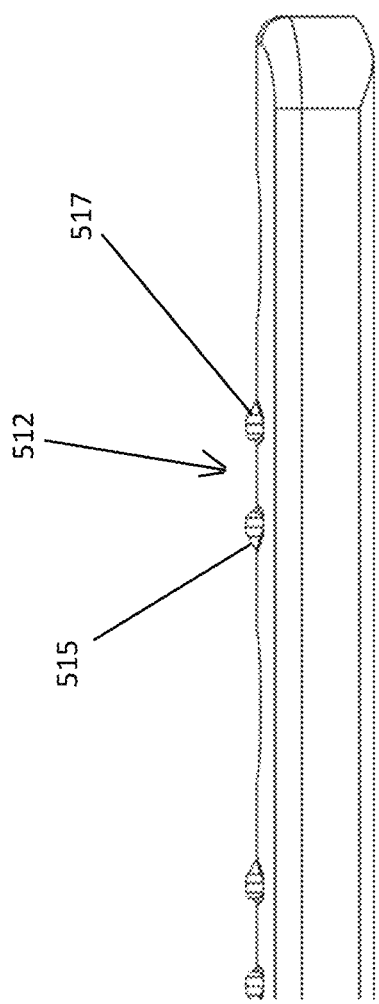
FIG. 23 is a close-up view of a portion of the plate of FIG. 20, including anti-migration projection.

In an example depicted in FIG. 19, a washer 400 may include lock bars 470 and an opening 440 for receiving screws therethrough to washer 400 to be fastened to a bone (e.g., bone 20). Washer 400 may be located at a desired point on a bone (e.g., bone 20) where no other hardware is placed or washer 400 may be located on a plate such that opening 440 is aligned with a hole of the plate to allow a screw to pass through opening 440 and the opening of the plate to connect washer 400 to such plate. A cord (e.g., cord 40) may be attached to lock bars 470 and lock bars or a hook of another washer, buckle or plate to hold portions of a bone (e.g., bone 20) together to reduce a fracture, for example. In other examples, lock bars may be integrated into other fracture fixation hardware, e.g., washers, plates, toothed washers, and bone anchors. Buckles in these cases may have both ends of a cord (e.g., cord 40) tape secured or the cord may be secured between two discrete pieces of hardware (e.g., first buckle 131, second buckle 132, and washer 400).

In another example depicted in FIGS. 20-23, a plate 500 is similar to plate 120 and may include a top side 505 opposite a bone contacting surface 507. A plurality of openings 540, similar to openings 140, may receive screws therethrough to allow plate 500 to be fastened to a bone (e.g., bone 20). Top side 505 may include a plurality of channels 510 bounded axially by anti-migration projections 520 on opposing axial sides thereof. For example, a first projection 515 and a second projection 517 of projections 520 may bound a channel 512 of channels 510. First projection 515 may have a first side 516 bounding channel 512 which is flat and extends about perpendicularly, relative to an axial dimension of plate 500, away from a bone contacting surface 507. Second projection 517 may have a second side 518 bounding channel 512 which is flat and extends about perpendicularly, relative to the axial dimension of plate 500, away from bone contacting surface 507. Channels 510 may be configured (e.g., axially shaped and dimensioned) to receive a cord or tape (e.g., cord 40) such that projections 520 (e.g., first projection 515 and second projection 517) inhibit or prevent movement of the cord or tape when received in channels 510 (e.g., channel 512) as depicted for example in FIGS. 24-25.

Figure 24:
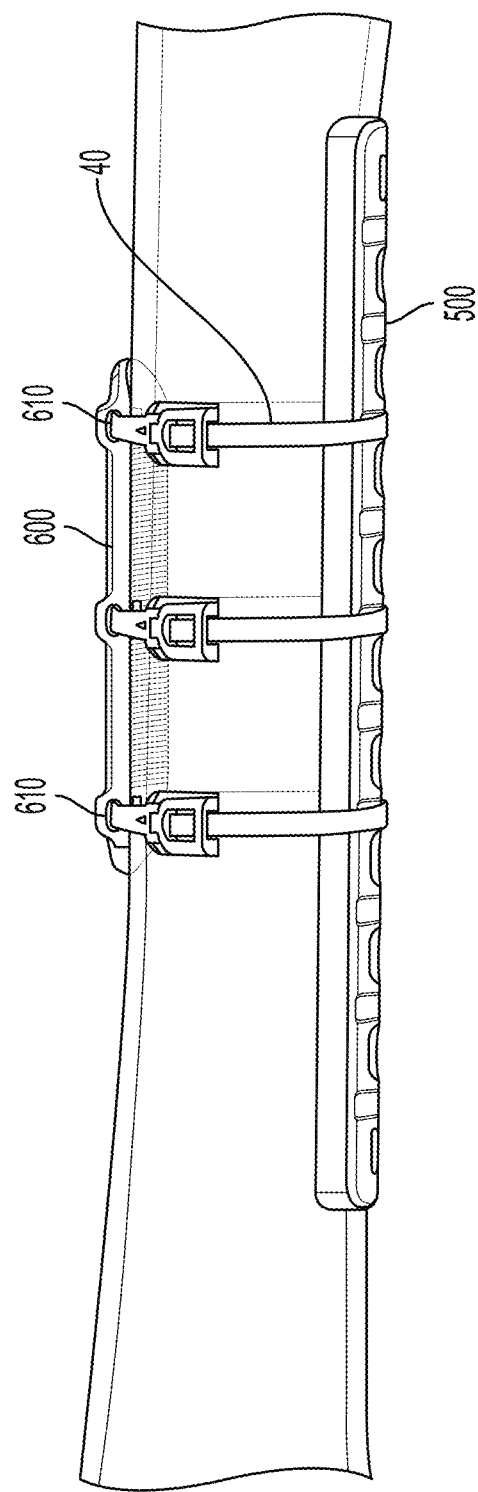
FIG. 24 is a side view of a system for fixating a bone utilizing the plate of FIG. 20.
Figure 25:
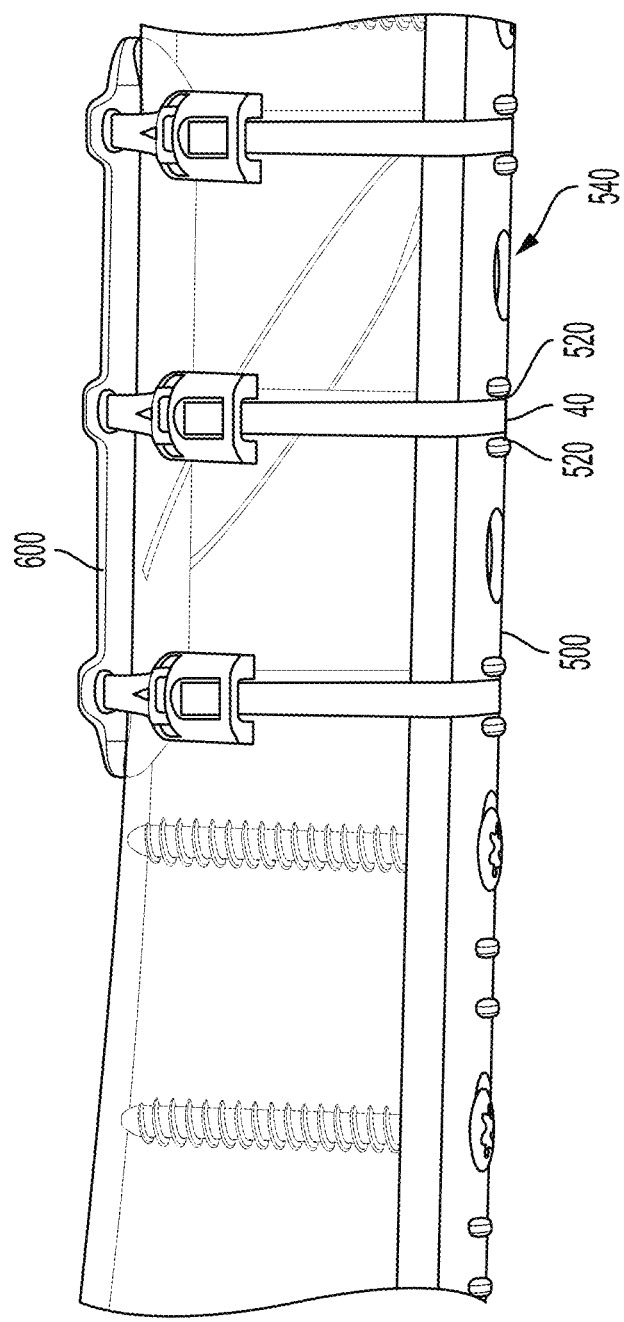
FIG. 25 is a close-up view of the system of FIG. 24, including screws through the plate of FIG. 20.

FIG. 24 depicts plate 500 being connected to a plate 600, similar to three-wire cerclage adjunct device 200 depicted in FIG. 17 and disclosed in co-owned U.S. Ser. No. 16/910,328 (our file no. 3768.085A) incorporated herein by reference, via multiple instances of cord 40 and buckles (e.g., buckle 300) with the cords being received in channels 510. Plate 600 may be shaped similar to the device in the co-owned application except that openings 610 in plate 600 through the device may be configured (e.g., shaped and dimensioned) to receive a cord or tape (e.g., cord 40). FIG. 25 depicts a close up of FIG. 24 while further depicting screws being received in openings 540 to connect plate 500 to bone 20. The screws may be inserted though openings 540 after one or more cords (e.g., cords 40) are fed through openings 610 in plate 600 and around plate 500 (e.g., contacting top surface 505) through channels 510 to secure and reduce a fracture in a bone (e.g., bone 20).

In an example, cord 40 may be passed around bone 20 as described above using passer 100. Cord 40 may be fed through openings 610 in plate 600 on an accessible side of bone 20 closest to a surgeon or user. Cord 40 may then be manipulated or pulled to move plate 600 to an opposite side of bone 20 such that plate 600 may be in a position as depicted in FIGS. 24-25 with plate 500 being located on an opposite side of bone 20. As indicated above, cord 40 may be located in channels 510 and multiple instances of cord 40 may be secured via multiple instances of buckle 30 as described above.

In an example, a tensioner 700 depicted in FIGS. 26-38 may include arms 710 with ends 720 configured (e.g., shaped and dimensioned) to receive a buckle (e.g., buckle 30 or buckle 300). For example, ends 720 may be configured to be received in slots 35 of buckle 30 as described above relative to tensioner 200. Arms 710 may be connected to a body 730 which may be connected to a rotatable tightener 740 configured to rotate relative to body 730 while attached to a cord (e.g., cord 40) to pull and provide tension to the cord while cord is around bone 20 as described above to facilitate the cord being secured around bone 20, plate 500 and plate 600, for example. A puller 750 located on an opposite end 752 of tensioner 700 relative to ends 720 may be connected to a cord (e.g., cord 40) after the cord is passed around bone 20, plate 500 and through plate 600 and puller may be pulled by a user to remove slack in cord 40 prior to tightener 740 being rotated to provide tension to cord to secure the cord and plates around bone 20 to fixate a fracture in bone 20, for example.

Figure 26:
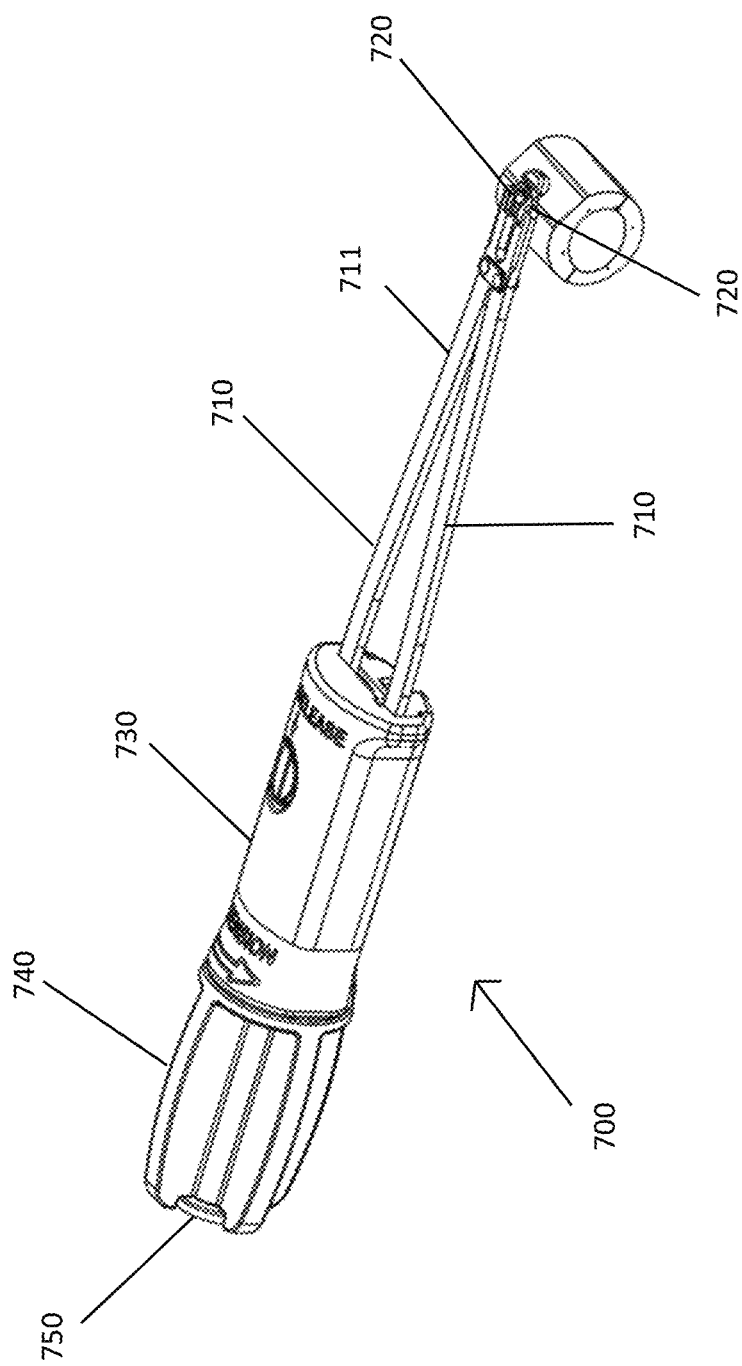
FIG. 26 is a perspective view of a tensioner engaged with a buckle and a bone to be fixated.
Figure 27:
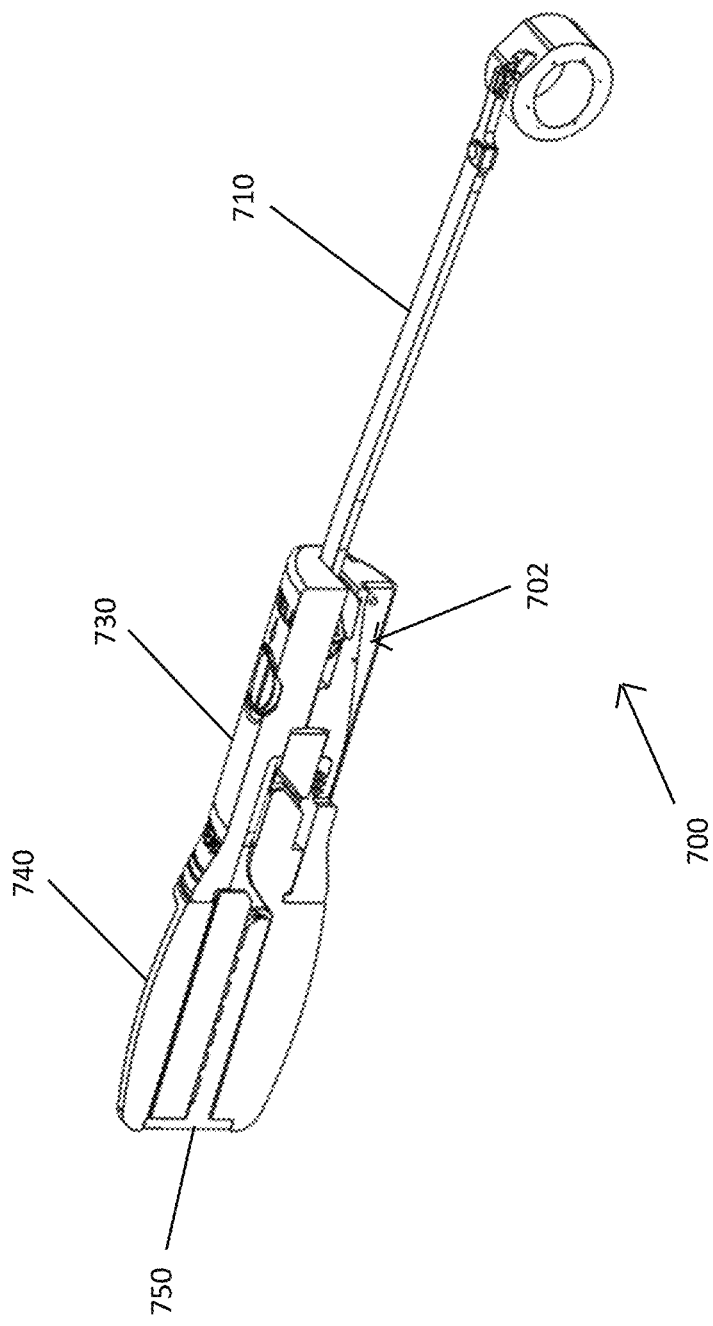
FIG. 27 is a side cross-sectional view of the tensioner of FIG. 26.
Figure 28:
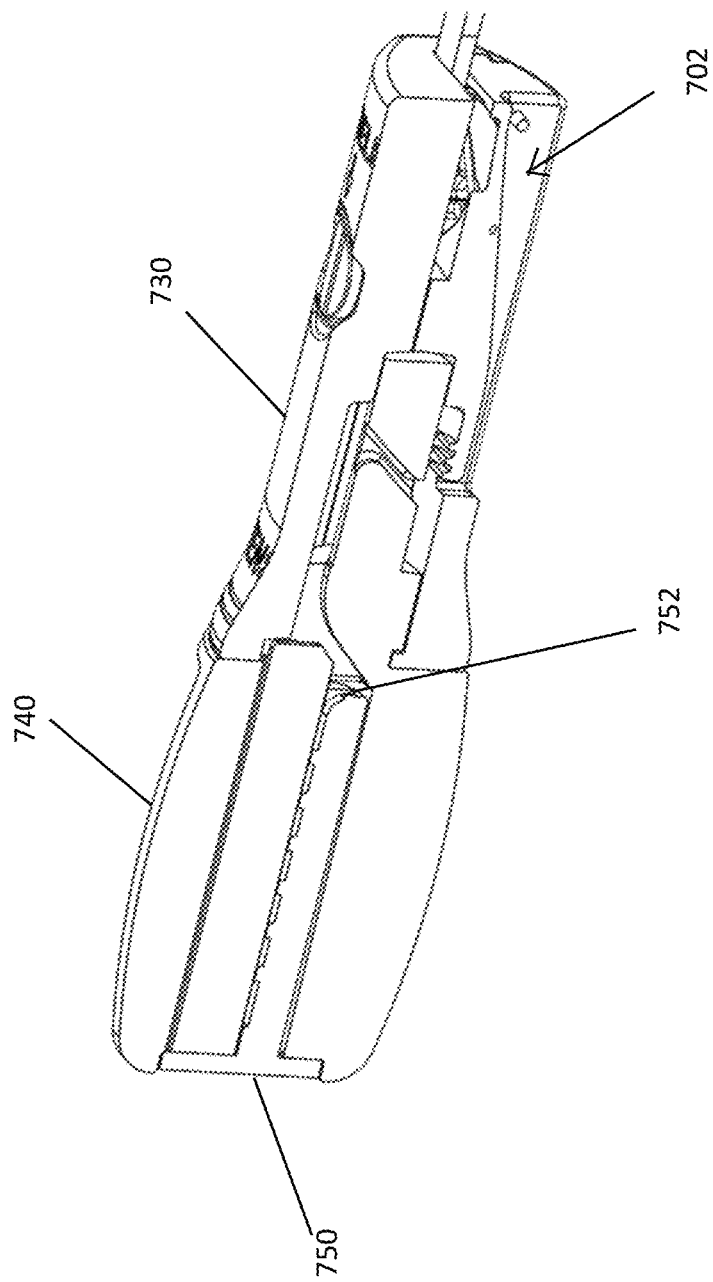
FIG. 28 is a close-up of a portion of the tensioner of FIG. 27.
Figure 29:
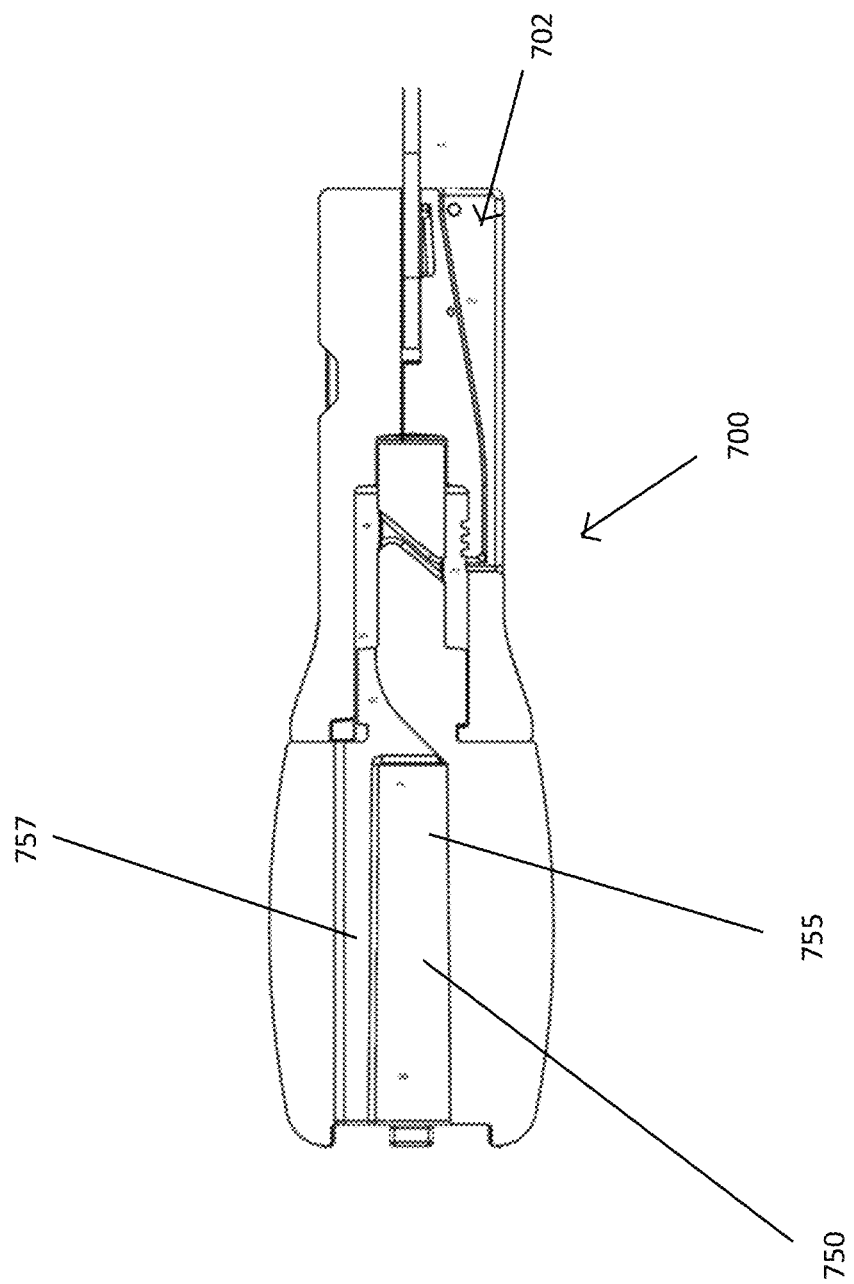
FIG. 29 is a side view of a portion of the cross-sectional view of FIG. 28.

FIG. 27 depicts a cross-sectional view of FIG. 26 while FIG. 28 is a close up of a portion of FIG. 27. FIG. 29 is a side-sectional view of FIG. 26 further showing cord 40 extending through an interior 702 of tensioner 700. Cord 40 extends along a path outlined by a path portion 1 to a path portion 2 to a path portion 3 to a path portion 4 to a path portion 5 to a path portion 6 to a path portion 7 to a path portion 8 to a path portion 9 through the interior 702 of tensioner 700.

Figure 30:
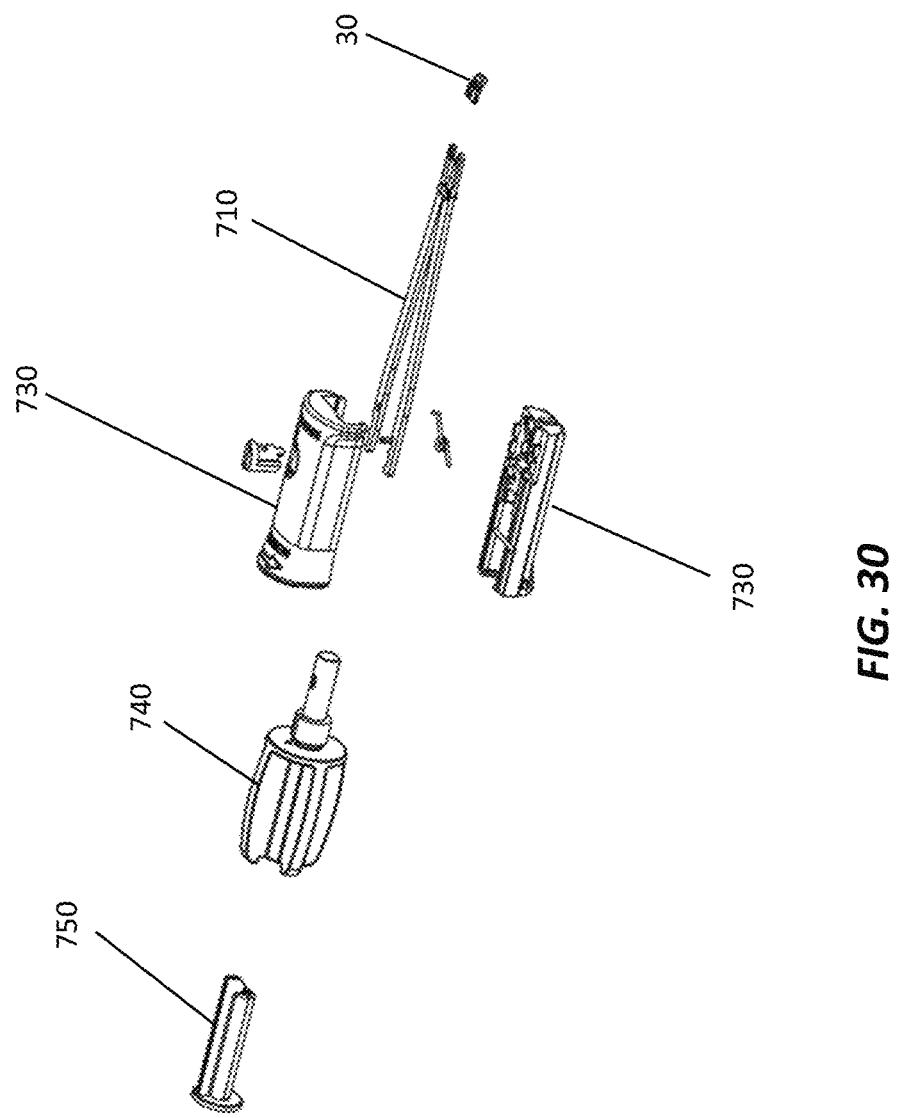
FIG. 30 is an exploded view of the tensioner of FIG. 26.
Figure 31:
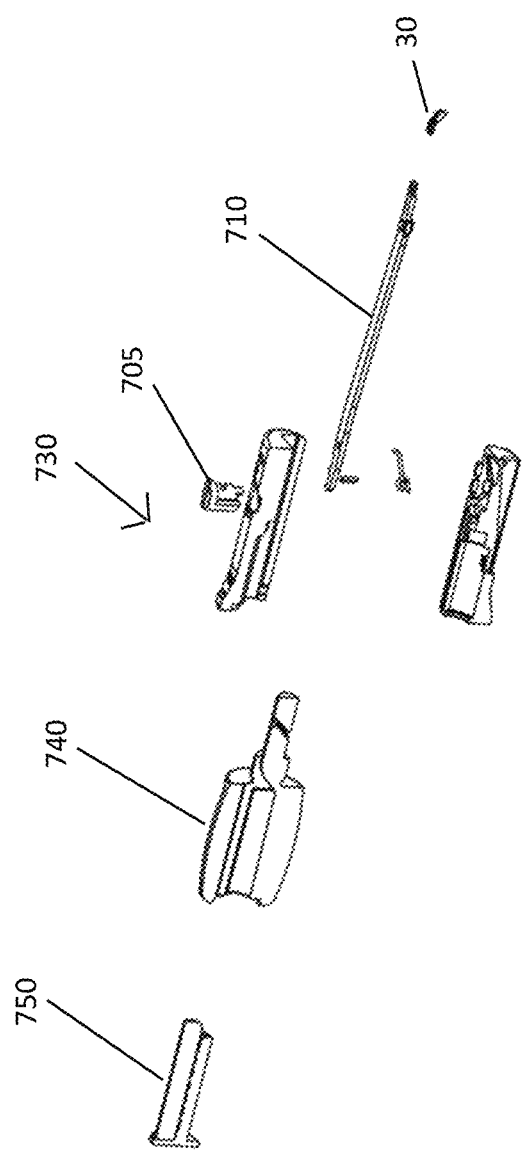
FIG. 31 is a cross-sectional view of the exploded view of the tensioner of FIG. 30.

FIG. 30 is an exploded view of tensioner 700 while FIG. 31 is a cross-section of the tensioner of FIG. 30.

Figure 32:
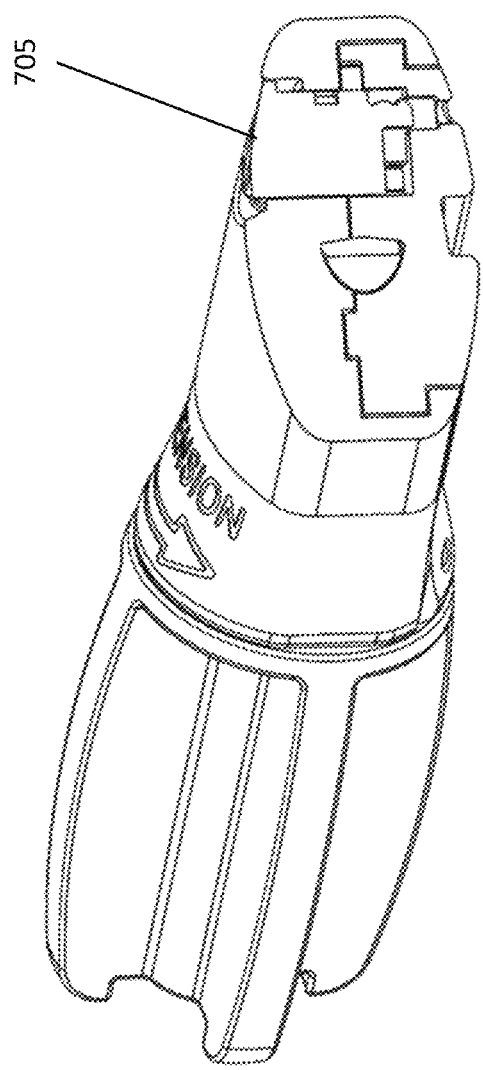
FIG. 32 is a cross-sectional view of the tensioner of FIG. 27 at an oblique angle relative to an axis of the tensioner showing a lock for arms of the tensioner in a locked position.

FIG. 32 depicts a cross-sectional view at an oblique angle relative to an axis of tensioner 700 showing an cut portion of body 730 depicting a position with a lock 705 in a release-locked position such that arms 710 are locked in a position holding a buckle (e.g., buckle 30). For example, the lock may maintain arms 710 in a particular position by inhibiting movement of the arms (e.g., proximal ends thereof) so that the arms (e.g., distal ends thereof) hold the buckle. In particular lock 705 may have a release slot 712 which is not aligned with an arm 711 of arms 710 in the locked position depicted in FIG. 32 thereby inhibiting movement of arms (e.g., proximal ends thereof) toward each to prevent release of the buckle.

Figure 33:
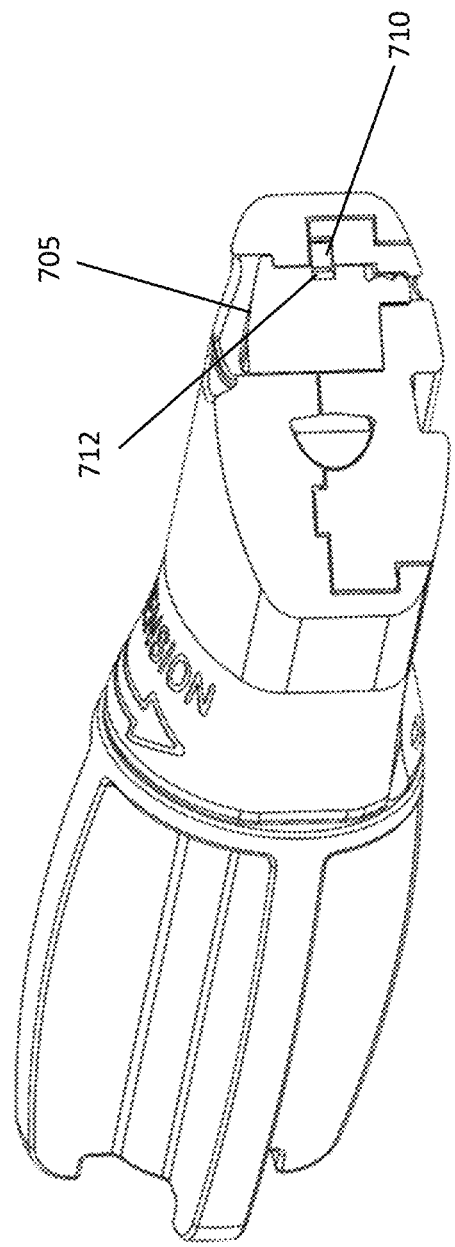
FIG. 33 is a cross-sectional view as in FIG. 32 with the lock in a non-engaged position.

FIG. 33 depicts the tensioner in FIG. 32 with lock 705 depressed toward the axis of tensioner 700, allowing arms 710 (e.g., proximal ends thereof) to move freely towards each other (and toward the axis of tensioner 700) to release a buckle held therein. In an example, a movement of lock 705 to the unlocked position depicted in FIG. 33 allows movement of arm 711 into release slot 712 inwardly toward the axis of tensioner 700 such that an opposite end of one or more of arms 710 (e.g., distal ends thereof) may move outwardly away from axis of tensioner 700 to allow a release of the buckle (e.g., buckle 30).

Figure 34:
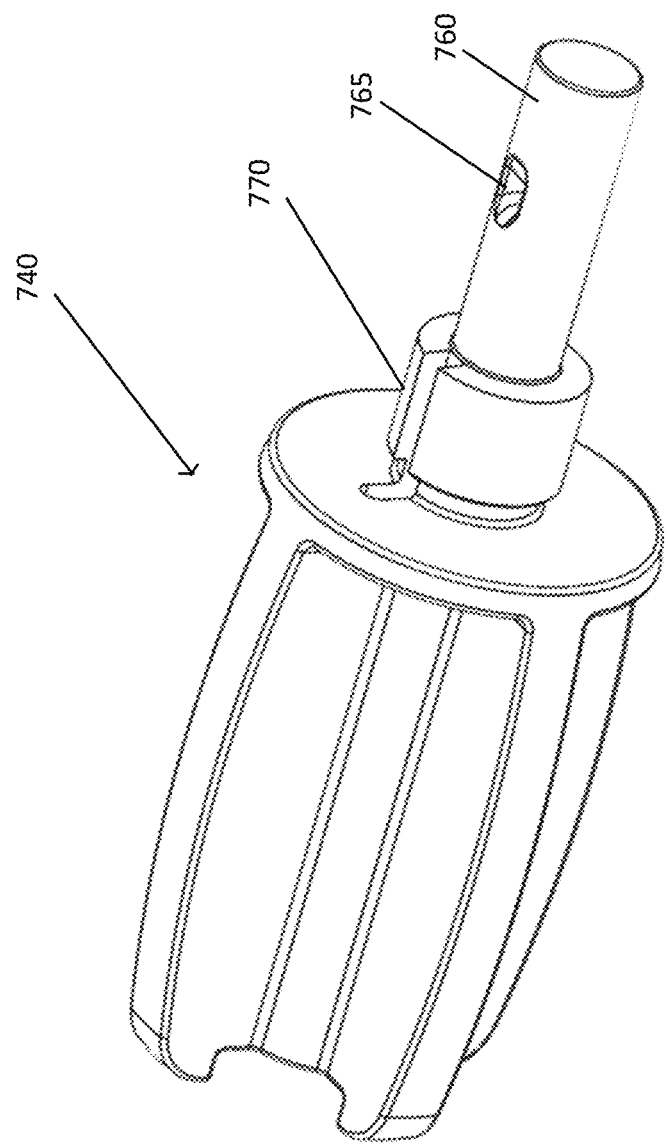
FIG. 34 is a perspective view of a tightener of the tensioner of FIG. 30.

FIG. 34 depicts rotatable tightener 740 separate from a remainder of tensioner 700 and includes a rod portion 760 having a rod opening 765 to allow cord 40 to pass from path portion 3 to path portion 4 as described above. A path channel 770 allows cord 40 to pass from path portion 4 to path portion 6.

Figure 35:
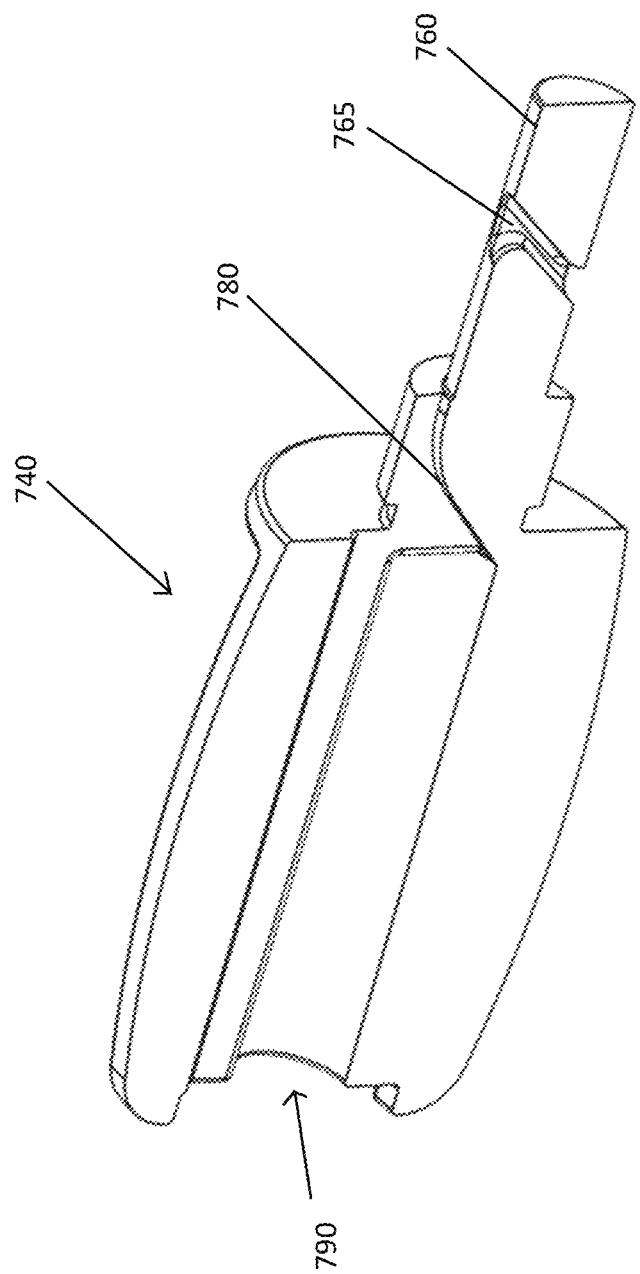
FIG. 35 is a cross-sectional perspective view of the tightener of FIG. 34.

FIG. 35 is a cross-section of FIG. 34 depicting opening 765 aligned non-perpendicularly relative to the axis of tensioner 700 such that a bottom end as depicted is closer to tightener 740 than a top end thereof. As shown, a second path channel 780 may extend from path channel 770 in an arc toward and past the axis of tensioner 700 and extending to a cavity 790 for receiving puller 750. Cord 40 may be received in cavity 790 after passing thorough the interior of tensioner 700 as described above and may be connected to puller 750 such that the surgeon or user may reduce or eliminate any slack in cord 40 prior to a rotation of tightener 740 to place tension on cord 40 and securing buckle 30 to cord 40 as described above.

Tightener 740 may provide tension on cord 40 due to the cord being received in opening 765 such that the rotation of tightener 740 causes cord 40 to be wrapped around rod 760 thereby pulling on cord 40 in a direction away from arms 710 toward puller 750. Such tension provided to cord 40 may allow a buckle (e.g., buckle 30).

Figure 36:
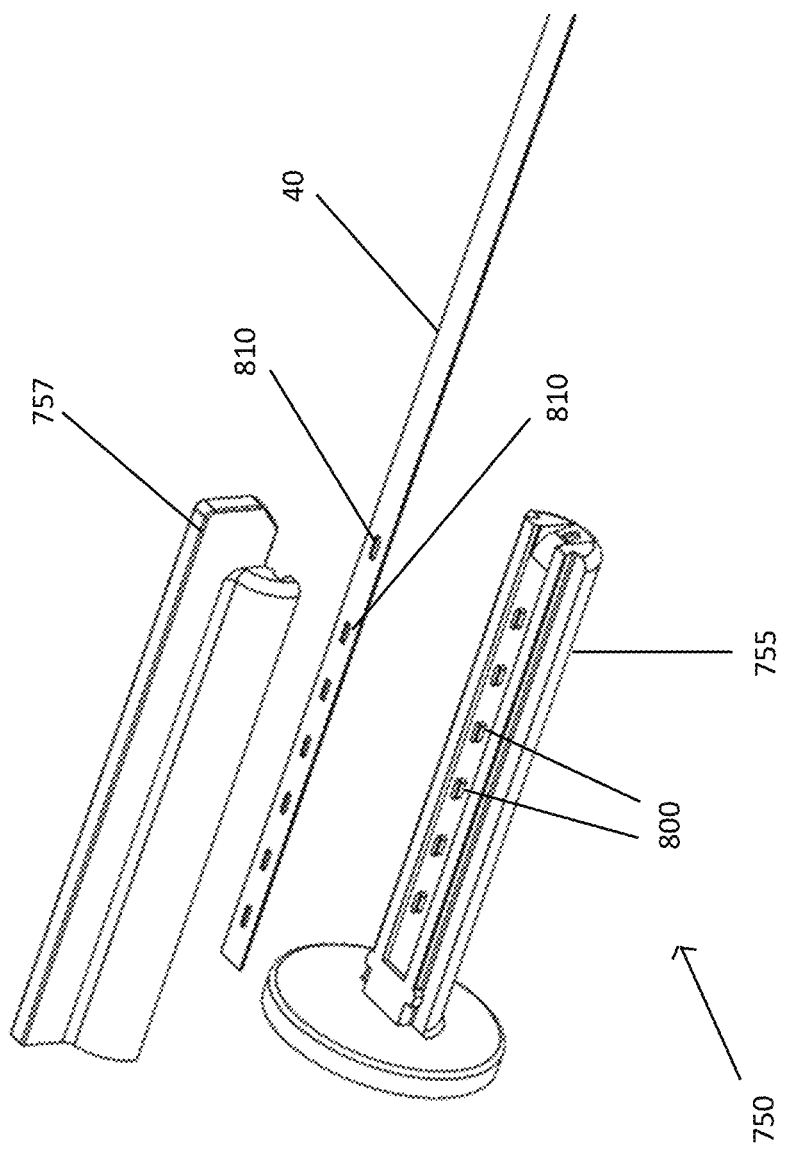
FIG. 36 is a perspective view of a puller of the tensioner of FIG. 30 exploded to show a connection of a cord to the puller.

FIG. 36 depicts puller 750 in an exploded view including puller body 755 and puller cap 757 with cord 40 therebetween. Puller body 755 may include connecting projections 800 configured (e.g., shaped and dimensioned) to be received in openings 810 of cord 40 to connect puller 750 to cord 40. Puller cap 757 may abut or be connected to puller body 755 to inhibit movement of cord 40 away from puller body 744 when connecting projections 800 are received in openings 810. Cord 40 may be fed through interior of tensioner 700 as described above. Further, cord may be fed between puller body 755 and puller cap 757 followed by the cap being connected to, or abutting puller body 755 when puller 750 is received in cavity 790 and/or when puller 750 is pulled out of cavity 790 when attached to cord 40 to provide a force to cord 40 to eliminate slack in cord 40 and/or to provide a tension to cord 40 to allow a buckle (e.g., buckle 30) to be secured to cord 40.

Figure 38:
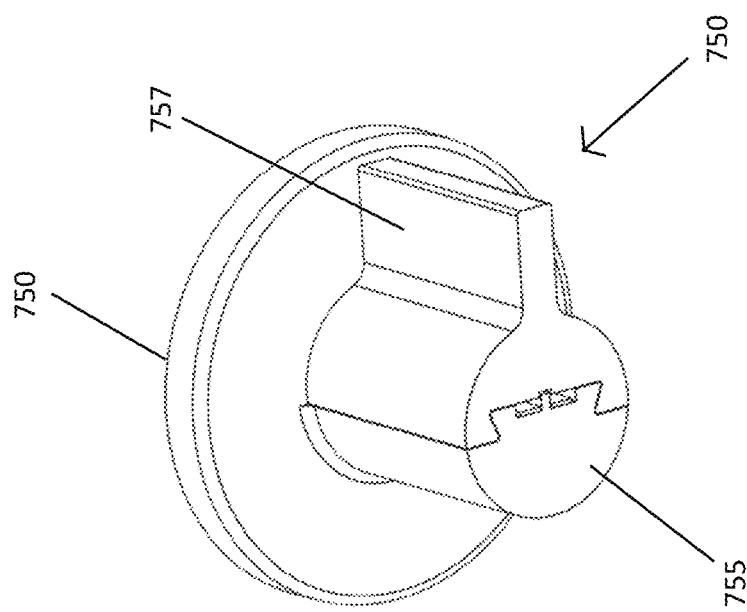
FIG. 38 is a perspective end view of the puller of FIG. 37.
Figure 37:
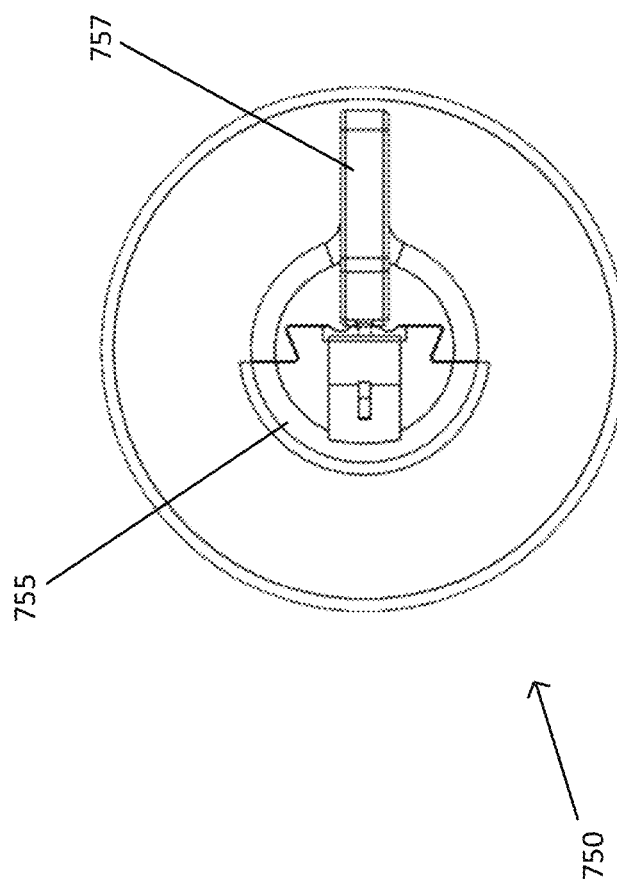
FIG. 37 depicts an end view of the puller of FIG. 36.
Figure 39:
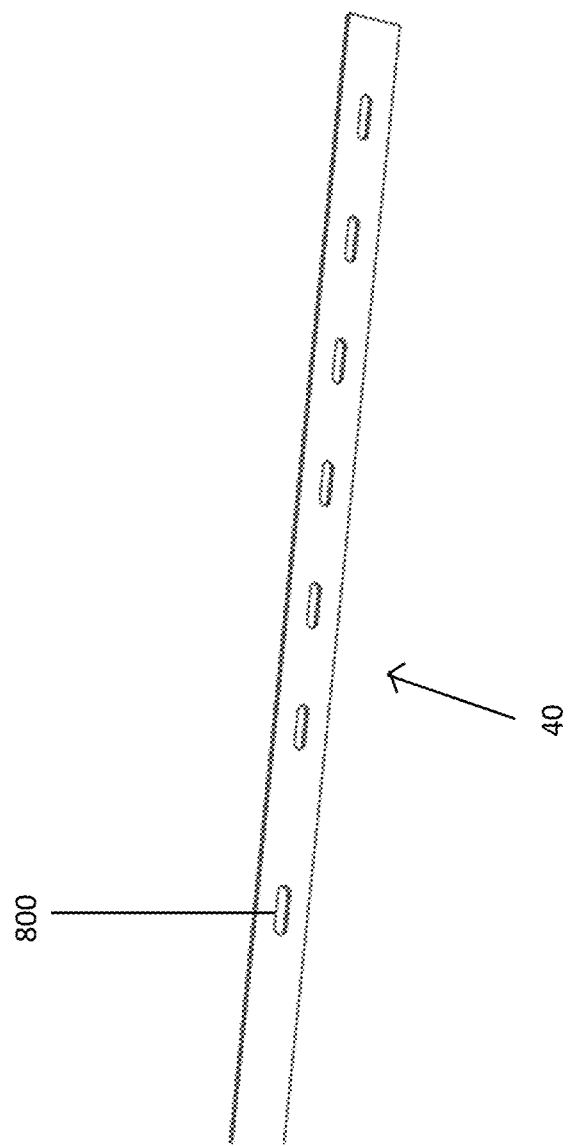
FIG. 39 is a top view of the cord of FIG. 36.

FIGS. 37 and 38 depict an end and perspective end view of puller body 755 and puller cap 757 engaged with cord 40 omitted from being shown therebetween.

FIG. 38 depicts a portion of cord 40 having laser cut holes for non-knotted termination (e.g., holes 800) as described above where connecting projections 800 are configured (e.g., shaped and dimensioned) to be received in openings 810 of cord 40.

In an undepicted example, puller cap 757 could include projections which may extend through a cord (e.g., cord 40) and into cavities into puller body 755 to hold the cord instead of the reverse described above. Further puller body 755 may engage puller cap 757 without projections on either puller body 755 or puller cap 757, via other connecting mechanisms, or merely via friction, to hold a cord therebetween when connected.

In an example, tensioner 700 may be used in a method for fixating a bone (e.g., bone 20). As described above, cord 40 may be passed around a bone (e.g., bone 20) as described above using passer 100. Cord 40 may be fed through openings 610 in plate 600 on an accessible side of bone 20 closest to a surgeon or user and around plate 500 (e.g., through channels 510). Cord may be connected to buckle 30 and arms 710 of tensioner 700 may be received in slots of buckle 30. Lock 705 may be in a locked position as depicted in FIG. 32 such that arms 710 are locked to hold buckle 30.

Proximal end 48 of cord 40 may be passed through interior 702 through rod opening 765 and into cavity 790 to connect to puller 750 as described above. The user or surgeon may pull on puller 750 to minimize slack in cord 40. Tightener 740 may be rotated to a put cord 40 connected to buckle 30 at a desired tension such that the buckle may hold the cord to allow a reduction of fracture 14, for example.

Although a particular path through tensioner 700 is described above, such a tensioner could include any arrangement where a path for a cord (e.g., cord 70) extends through a tensioner to allow the cord to be pulled (e.g., via pulling by a person) to minimize slack and rotated (e.g., via a rotatable rod having an opening to receive the cord) to provide tension on a bone, the cord and any plates used to fixate a fracture. Further, although tensioner 700 is described as connected to buckle 30, the tensioner could be utilized with buckle 300, or any buckle configured for use in the fixation method described and having slots configured for engaging arms 710.

Figure 40:
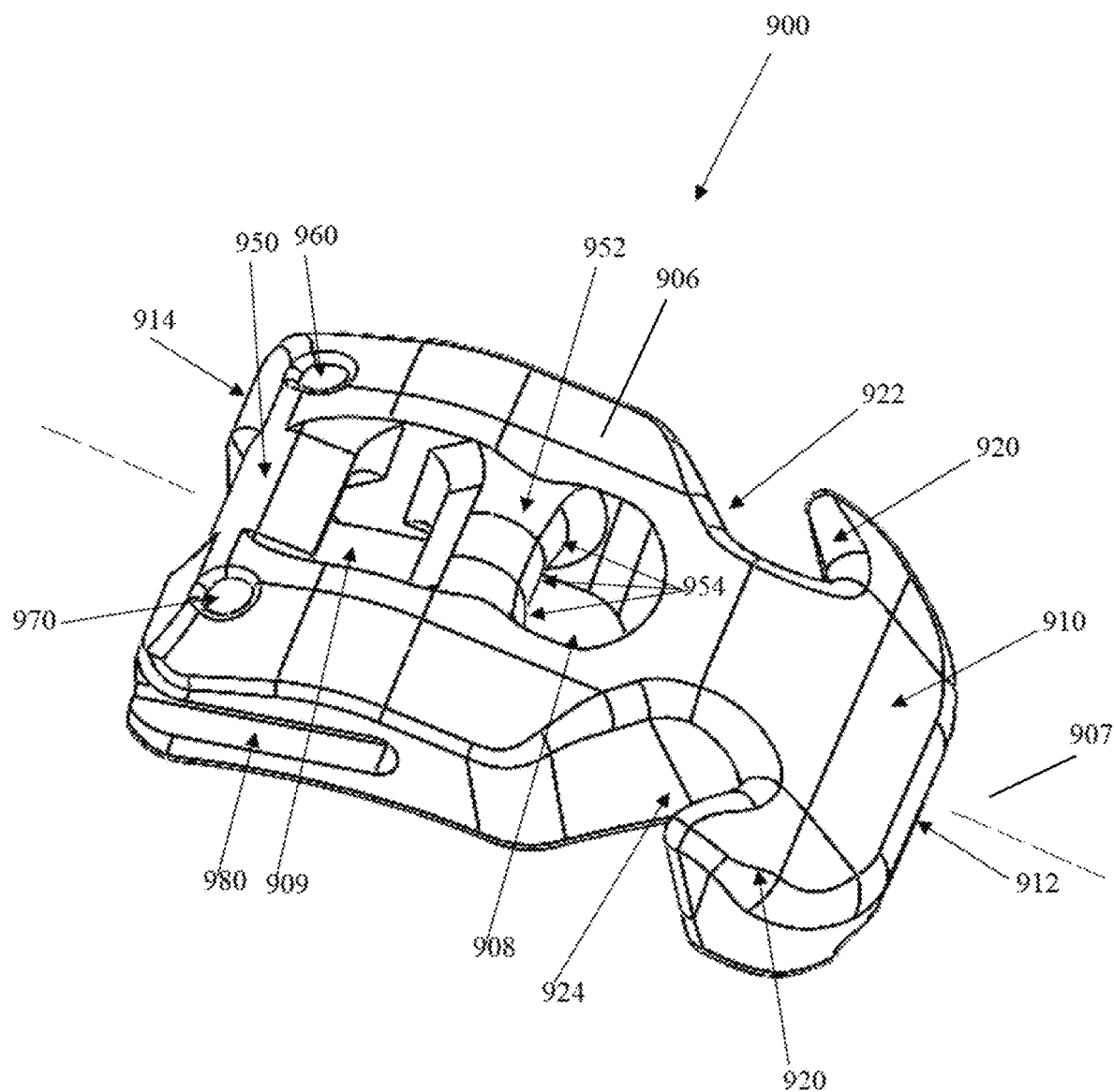
FIG. 40 is a perspective view of another example of a buckle useful in place of the buckle of FIGS. 1 and 15.
Figure 41:
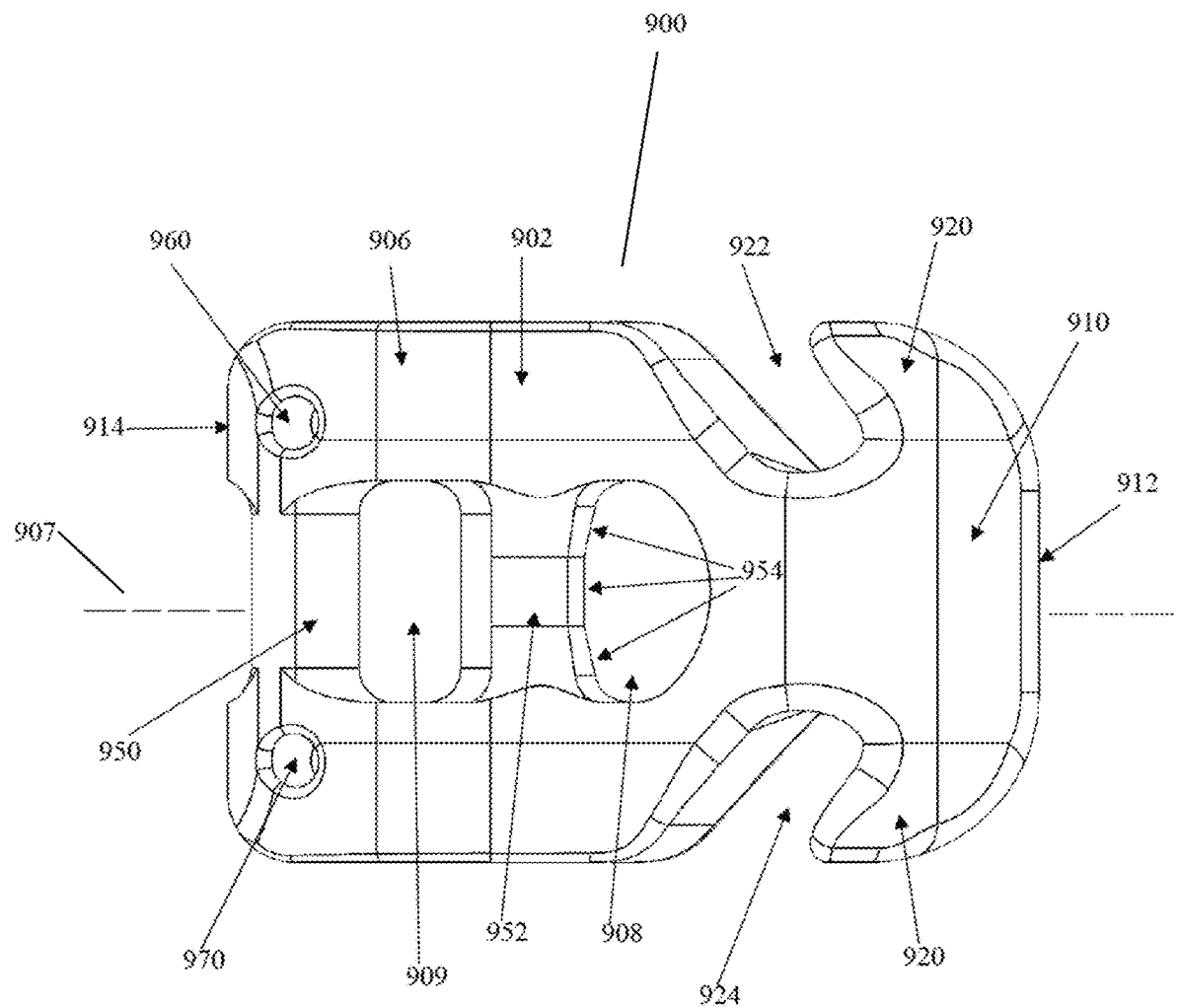
FIG. 41 is a top view of the buckle of FIG. 40.
Figure 42:
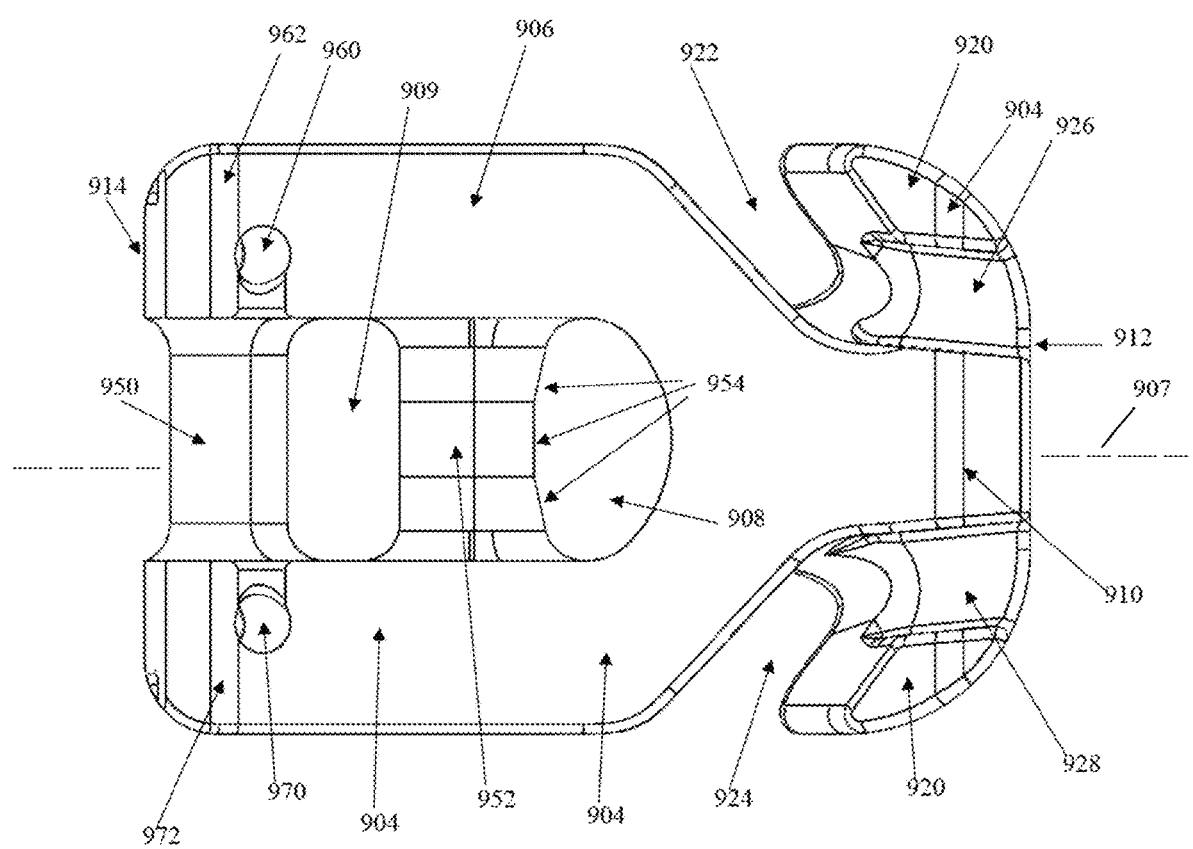
FIG. 42 is a bottom view of the buckle of FIG. 40.
Figure 49:
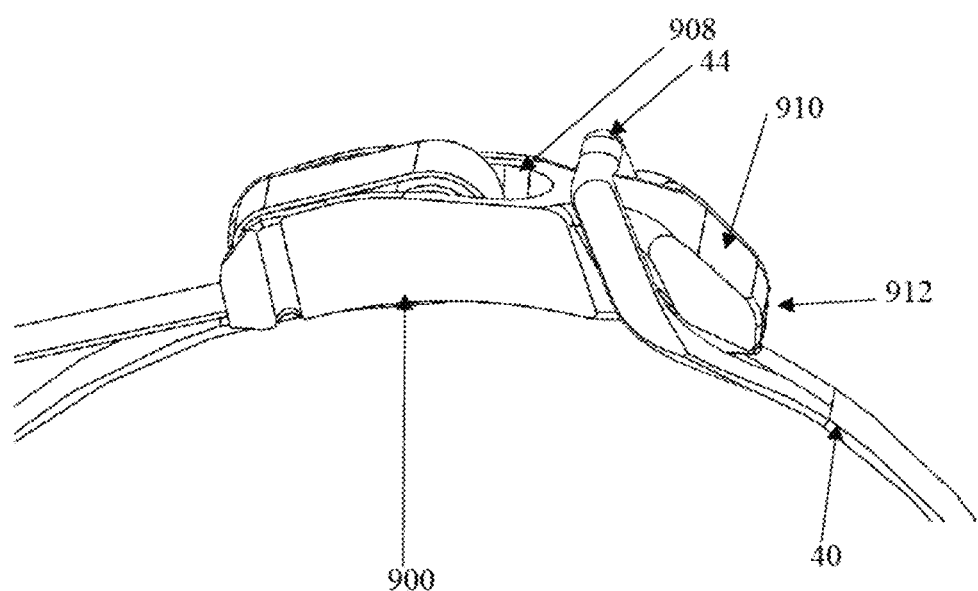
FIG. 49 is a perspective side view of a buckle of FIG. 40 holding a cord.

FIGS. 40-42 depict another example of a buckle 900 that may be utilized in place of buckles 30 or 300 described above. Buckle 900 includes a body 906 having a longitudinal axis 907. Body 906 includes a proximal end 914 and a distal end 912. A hook or loop 910 extends towards distal end 912. Lock members 950, 952 extend perpendicular to longitudinal axis 907 between portions of body 906 forming slot 908 between lock member 952 and hook 910 and slot 909 between lock members 950 and 952. Lock members 950, 952 may be utilized to connect to cord 40 as described above for lock bars 70 and 350 and shown in, for example, FIG. 49.

Figure 47:
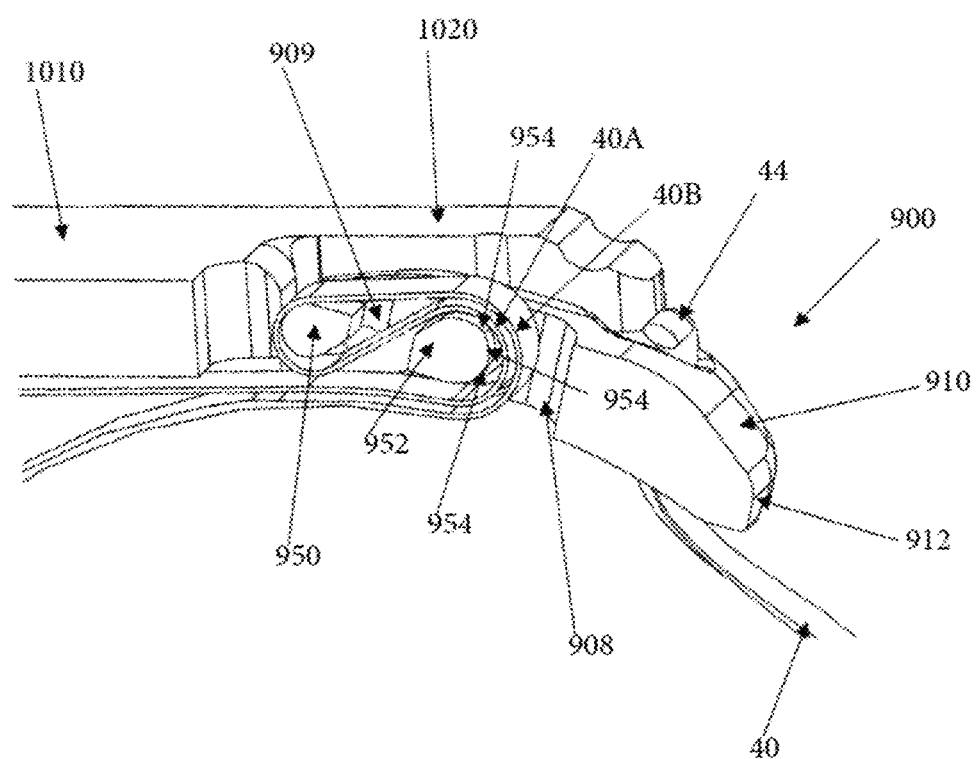
FIG. 47 is a partial cross-sectional view of one example of a distal end portion of a tensioner depicted in FIG. 43 holding a buckle of FIG. 40 and a portion of a cord passing through the buckle.

In an example, interior lock bar 952 may include an engagement surface 954 configured to receive overlapping portions of cord 40 passing through the second slot (see FIG. 47). Engagement surface 954 defines a proximal end surface of second slot 908 that is concave in the longitudinal direction of body 906 as it extends along the lateral direction (e.g. perpendicular to longitudinal axis 907) of interior lock bar 952. In one example, engagement surface 954 is arcuately concave in the longitudinal direction as it extends along the lateral direction of interior lock bar 952. Engagement surface 954 is configured to receive and contain or maintain cord 40 centralized on interior lock bar 952 during tensioning to ensure that the tensioned cord 40 stays in the middle of interior lock bar 952 and does not get bunched up. This configuration also, for example, prevents stacked or overlapping portions 40A and 40B of cord 40 (see, e.g., FIG. 47) from migrating away from each other and getting tangled or jammed. Engagement surface 954 ensures that cord 40 is centralized and stays in the middle of interior lock bar 952. In the past, an interior lock bar was generally cylindrical in the lateral direction, or perpendicular to longitudinal axis 907, having a constant cross-section from its centerline to the edges that contact body 906. The past configuration resulted in stacked portions of cord 40 migrating away from each other and becoming bunched up. Engagement surface 954 centralizes cord 40 by, for example, pushing or guiding cord 40 towards the center (e.g. near longitudinal axis 907) of interior lock bar 952.

As depicted in FIGS. 40-42, buckle 900 may include a hook or loop 910 at distal end 912. Hook 910 comprises two outwardly facing prongs 920 configured to be attached to loop 44 of cord 40 (see e.g. FIG. 49). Prongs 920 each form a loop engagement space 922, 924 with portions of body 906. As illustrated in FIG. 42, loop engagement spaces 922, 924 may communicate with loop engagement channels 926, 928 formed on the bottom surface 904 of buckle 900. Loop engagement channels 926, 928 extend from loop engagement spaces 922, 924 out distal end 912 of buckle 900. Loop engagement channels 926, 928 are converging to, for example, make loop 42 of cord 40 sit lower on the bone to require less bending of the tape fibers. Loop engagement channels 926, 928 are also canted to reduce the angle at which the loop fibers must adapt to, resulting in a longer life cord and lower profile construct. In past configurations, a cord wrapped around hooks and the bottom surface of a buckle would prop the buckle up off the bone where a patient would notice. This past configuration put extra stress on the cord resulting from bending of the cord to go around the hook. By passing cord 40 through loop engagement channels 926, 928, buckle 900 is able to be positioned closer to or lower on the bone while avoiding any bending of cord 40, resulting in a stronger hold (e.g. straighter cord is stronger than a bent cord).

As shown in FIGS. 41 and 42, buckle 900 may also include two retainer holes 960, 970 positioned close to the outer corners at the proximal end 914 of buckle 900. Retainer holes 960, 970 extend from top surface 902 of buckle 900 through to bottom surface 904 of buckle 900. In one example depicted in FIG. 42, retainer holes 960, 970 communicate with connection channels 962, 972, respectively, that extend laterally along proximal end 914 and perpendicular to longitudinal axis 907. Retainer holes 960, 970 with connection channels 962, 972 are pathways for a flexible cord or suture (not shown) that assist in holding buckle 900 to tensioner 1000 during transport and installation, as will be described in more detail below. Similar to loop engagement channels 926, 928, connection channels 962, 972 prevent the flexible cord or suture from propping up buckle 900 and allow buckle 900 to be positioned closer to or lower on the bone.

Figure 43:
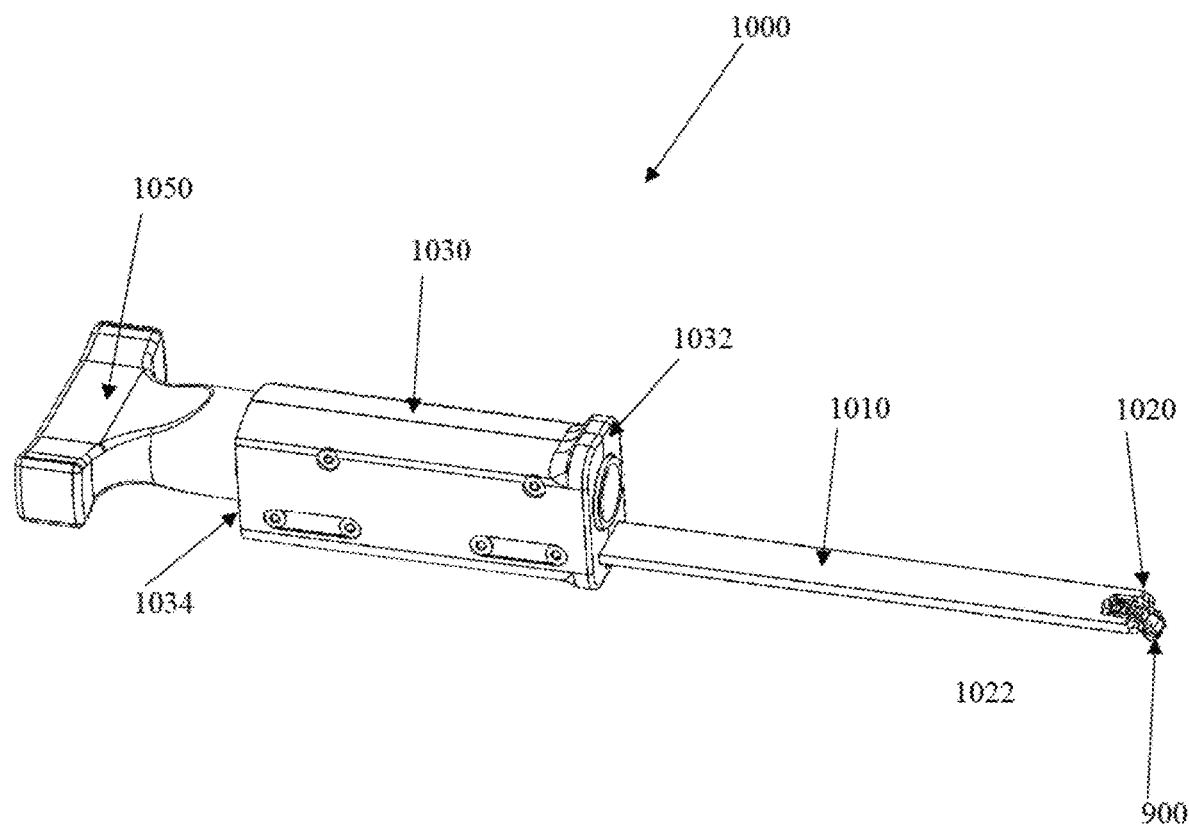
FIG. 43. is a perspective view of an example of an tensioner engaged with a buckle such as the one depicted in FIG. 40.
Figure 44:
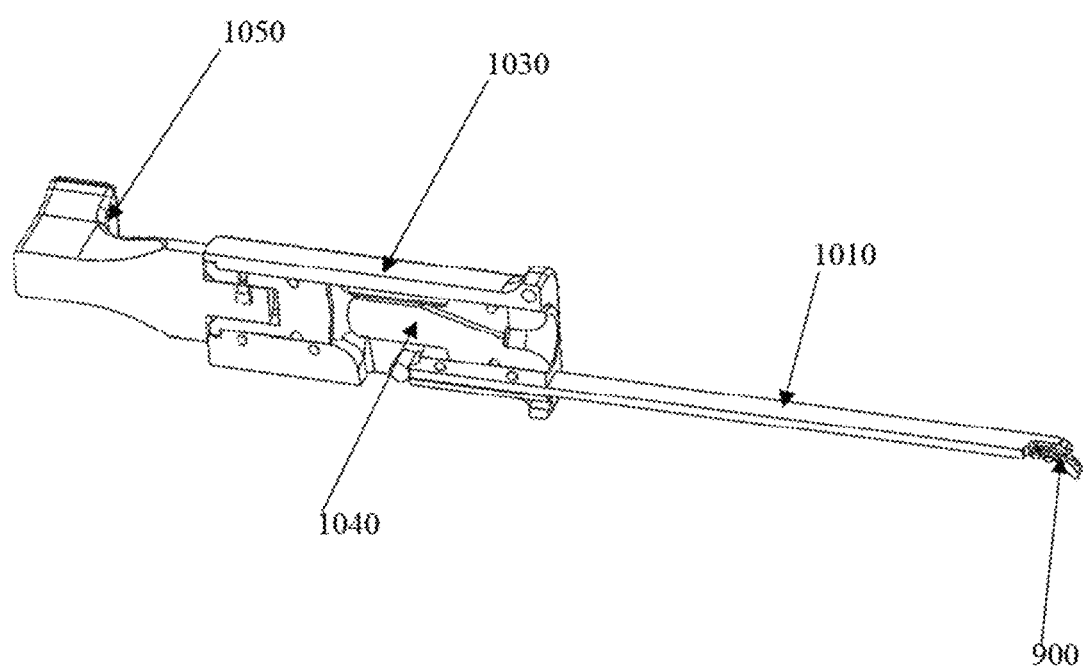
FIG. 44 is a longitudinal cross-sectional view of the tensioner of FIG. 43.
Figure 45:
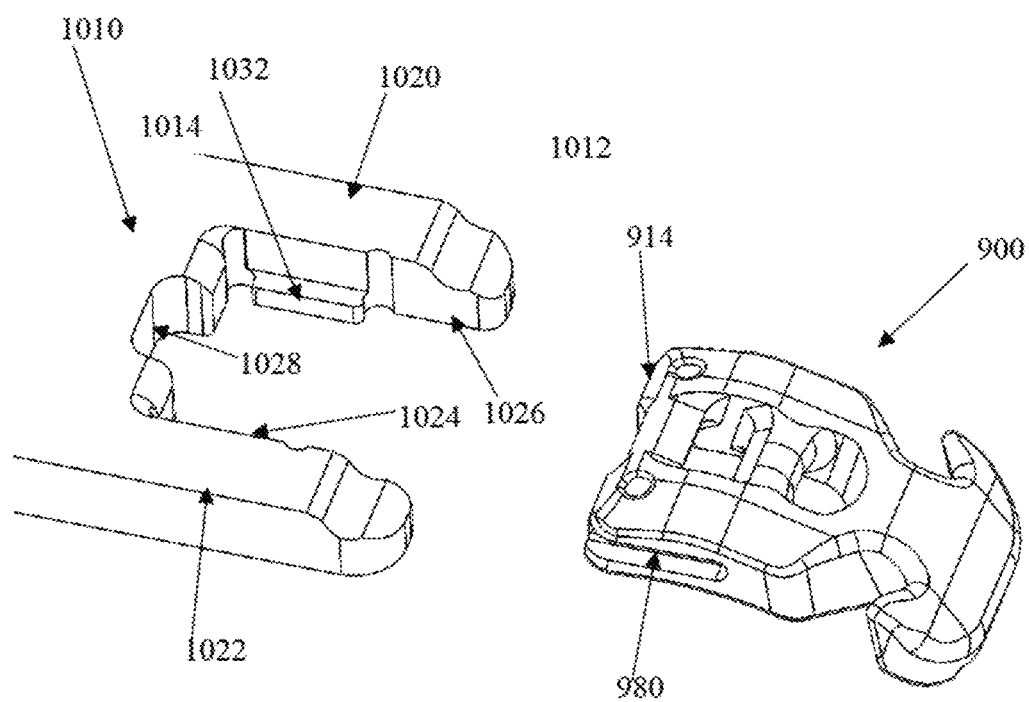
FIG. 45 is a partial perspective views of one example of a distal end portion of a tensioner depicted in FIG. 43 and the buckle of FIG. 40.

In an example, a tensioner 1000 depicted in FIGS. 43-45 is used to insert buckle 900 and tighten cord 40 in relation to buckle 900 around a bone. Tensioner 1000 may, in one example, include a housing 1030, an arm 1010 extending out a proximal end 1032 of housing 1030, and a removeable handle 1050 extending out of a distal end 1034 of housing 1030. In one example, arm 1010 includes a distal end 1012 configured (e.g. shaped and dimensioned) to receive a buckle (e.g. buckle 900). As illustrated in the embodiment depicted in FIG. 45, distal end 1012 of arm 1010 may include two extending fingers 1020, 1022 defining a U-shaped loading recess 1014. U-shaped loading recess 1014 is open to, for example, receive proximal end 914 of buckle 900. U-shaped loading recess 1014 is defined by interior walls 1024, 1026 of fingers 1020, 1022 respectively, and end surface 1028.

Each finger 1020, 1022 includes a capture boss 1032 extending longitudinal along interior walls 1024, 1026 of fingers 1020, 1022 and inwardly into U-shaped loading recess 1014. During loading of buckle 900 into tensioner 1000, U-shaped loading recess 1014 receives proximal end 914 of buckle 900. As proximal end 914 of buckle 900 is slid into U-shaped recess 1014, recesses 980 formed in the sides of body 906 of buckle 900 extending longitudinally along body 906 from proximal end 914 engage capture bosses 1032. Once inserted, buckle 900 may be held by tensioner 1000 by, for example, a slip fit between capture bosses 1032 and recesses 980.

In one example, a flexible cord or suture (not shown) may assist in holding buckle 900 to tensioner 1000 during transport and insertion. Flexible cord or suture may be passed through retainer holes 960, 970 and connection channels 962, 972 formed in bottom surface 904 of body 906 of buckle 900 and attached to, for example, arm 1010 by, in one embodiment, passing through one or more through holes (not shown) formed near the distal end of arm 1010, and tied off.

Figure 46:
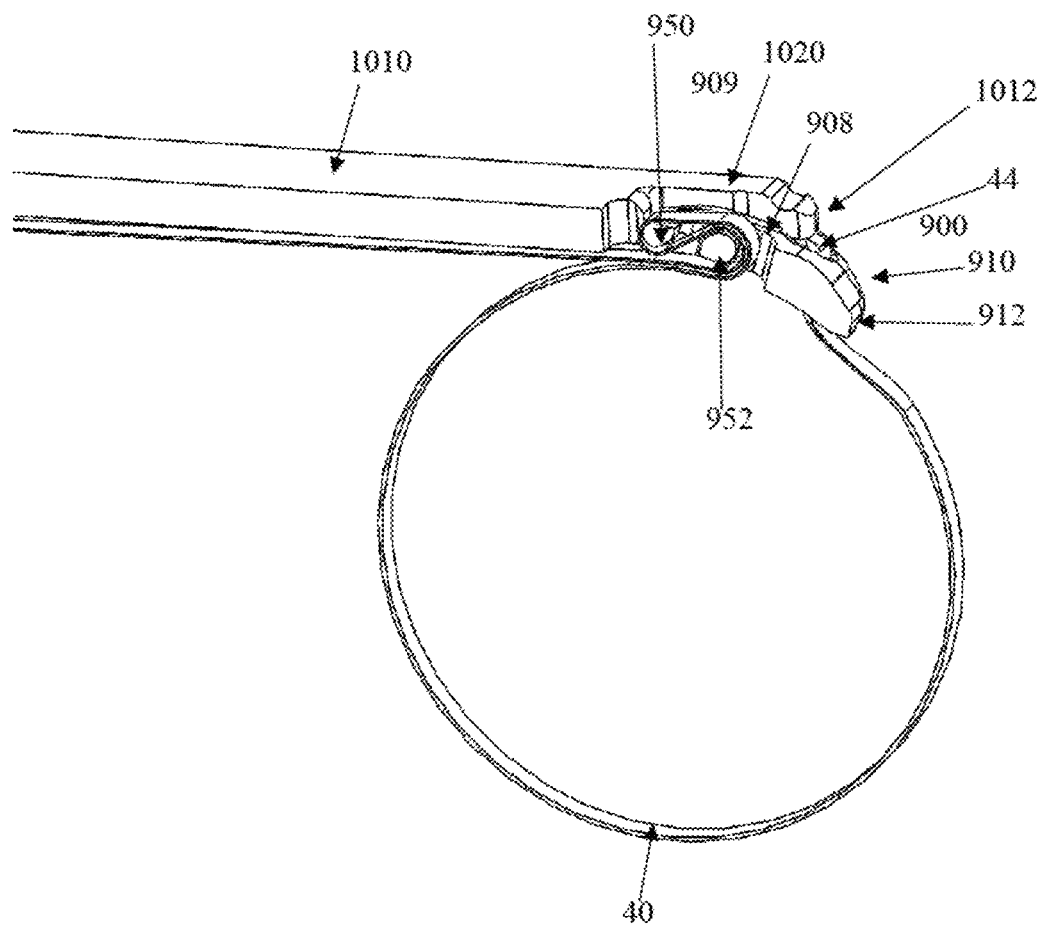
FIG. 46 is a partial cross-sectional view of an example of a distal end of a tensioner depicted in FIG. 43 holding the buckle of FIG. 40 and a portion of a cord passing through the buckle and forming a loop for surrounding a bone.
Figure 48:
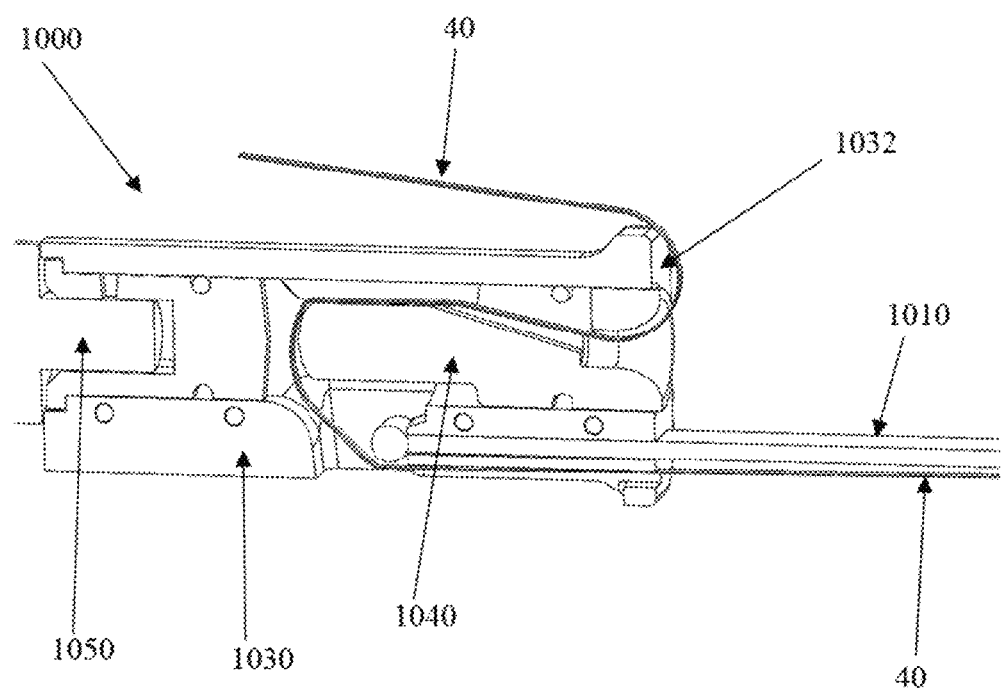
FIG. 48 is a partial cross-sectional view of one example of a tensioner depicted in FIG. 44 illustrating a pathway of a cord passing therethough.

FIGS. 46-48 illustrate one example of a pathway for cord 40 around a bone, through buckle 900 and in tensioner 1000. As depicted in FIGS. 46-47, loop 44 of cord 40 is attached to hook 910, looped around the bone and engaged with locking members 950, 952 of buckle 900. In one example, cord 40 passes into slot 908 through bottom side 904, contacting and centrally located by engagement surface 954 and out top side 902 of buckle 900. Cord 40 is then passed over lock member 952 and around lock member 950 at the proximal end 914. Cord 40 then passes up into slot 909 through bottom side 904, through slot 909, out top side 902, and then back around lock member 952. While wrapping around portions of lock member 952, cord 40 engages with and is centrally located by engagement surface 954. As depicted in FIG. 47 overlapping cord portions 40A and 40B extend into and through slot 908 while cord portion 40A directly contacts engagement surface 954. Cord 40 then passes out slot 908 through bottom side 904 of buckle 900 and back towards proximal end 914 and away from distal end 1012 of arm 1010 towards housing 1030 of tensioner 1000.

FIG. 48 illustrates one example of a pathway of cord 40 through housing 1030 of tensioner 1010. In this example, cord 40 passes into housing 1030 through proximal end 1032 and beyond the end of arm 1010 and into a rotatable member 1040 and then back out distal end 1032. The free end of cord 40 is then accessible to a surgeon to grab and pull or provide tension to tighten cord 40 around the bone through buckle 900.

Figure 50:
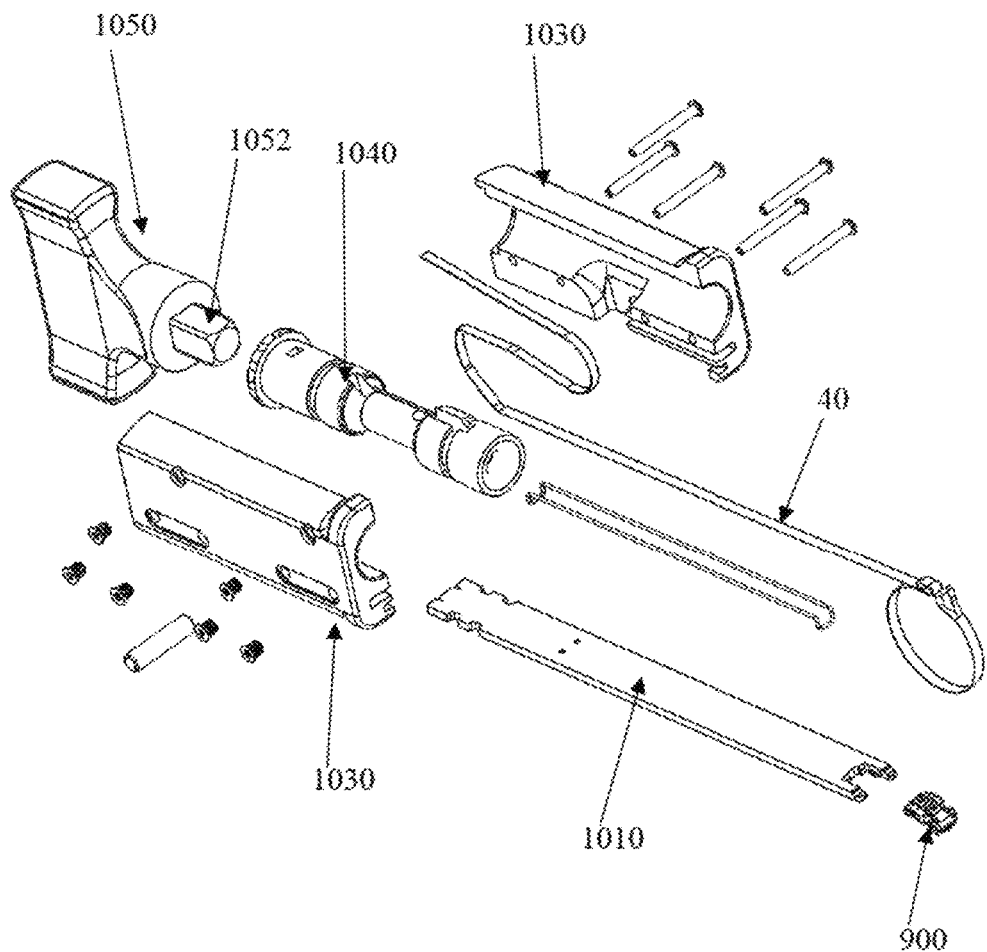
FIG. 50 is an exploded view of one example of a tensioner depicted in FIG. 42, a buckle depicted in FIG. 40 and a cord passing through the buckle.
Figure 52:
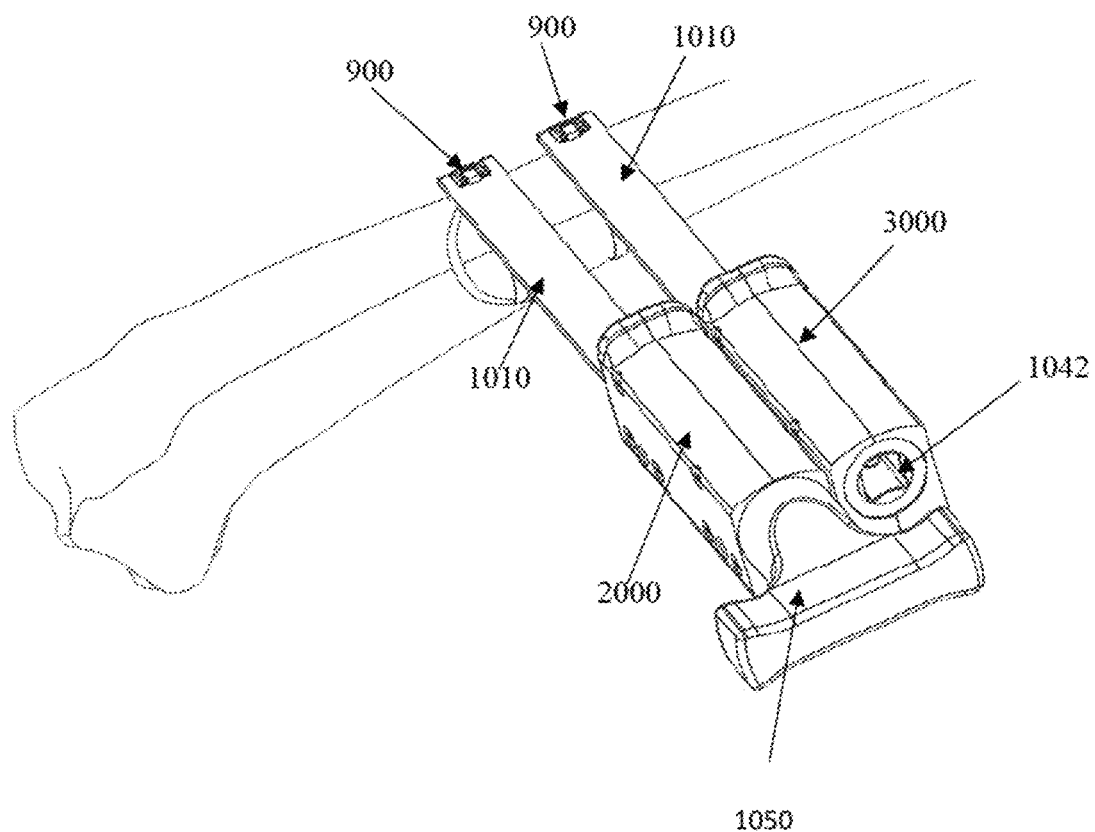
FIG. 52 is an end perspective view of the two side by side tensioners of FIG. 50.

Removable handle 1050 of tensioner 1000 is configured to allow a surgeon to hold tensioner 1000 with one hand while pulling cord 40 exiting distal end 1032 of housing 1030 of tensioner 1000 with the other hand. Removeable handle 1050 may also be rotatable relative to housing 1030 and engageable with rotatable member 1040 rotatable housed within housing 1030 to cause simultaneous rotation of rotatable member 1040 within housing 1030 to twist a portion of cord 40 passing through rotatable member 1040 to provide additional tension to cord 40 passing through buckle 900. As illustrated in FIGS. 50 and 52, rotatable member 1040 includes a cavity 1042 configured to receive a mating end 1052 of handle 1050 to allow simultaneous rotation of rotatable member 1040 as handle 1050 is rotated.

When a bone fracture is pulled together and the surgeon is content with the bone reduction, cord 40 is cut near the distal end 1012 of arm 1010 of tensioner 1000 behind proximal end 914 of buckle 900. The flexible cord or suture passing through retainer holes 960, 970 and attached to distal end 1012 of arm 1010 that assists in securing buckle 900 to tensioner 1000 during transport and installation may also be cut to free buckle 900 from tensioner 1000.

Figure 51:
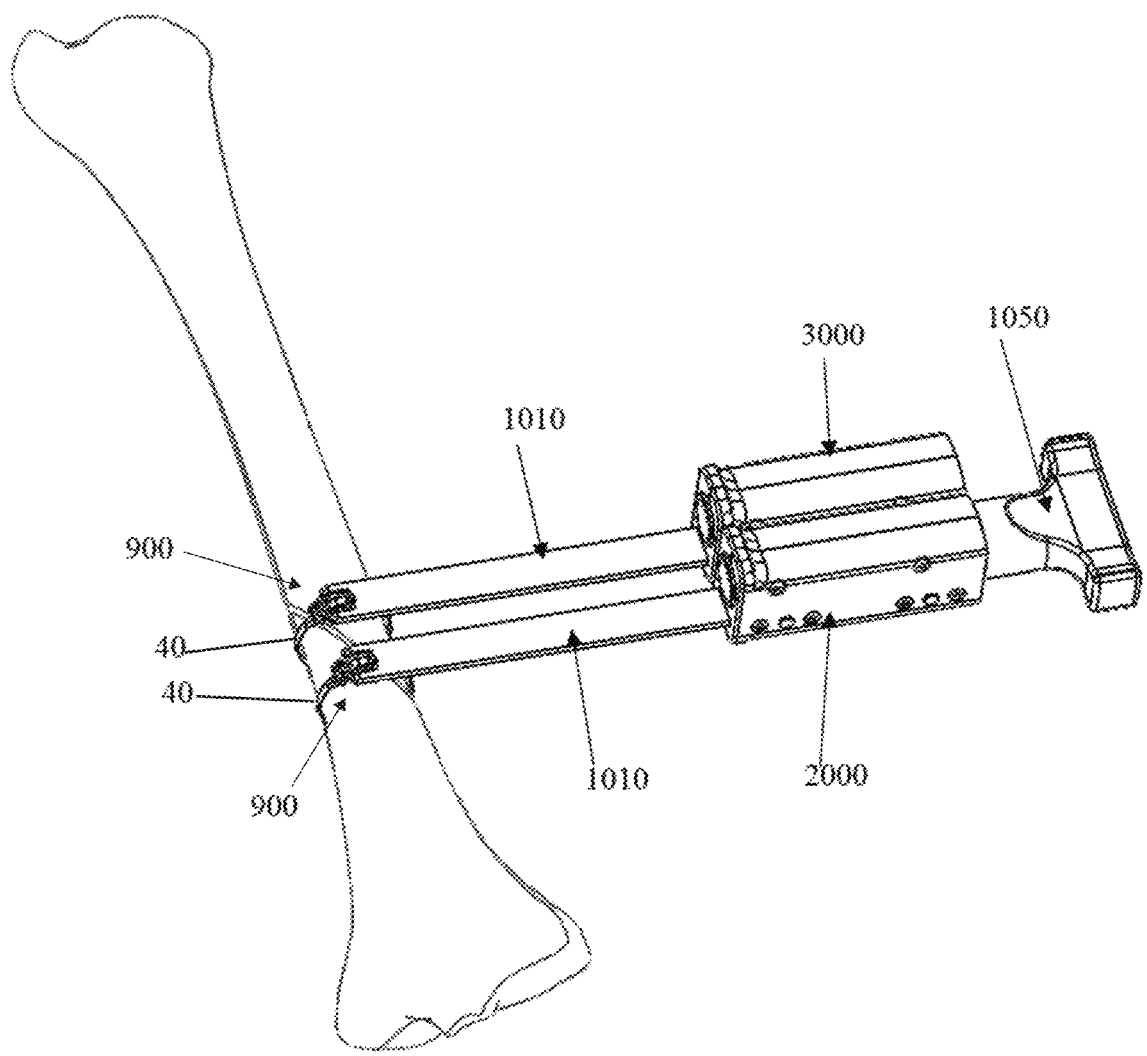
FIG. 51 is a top perspective view of two side by side tensioners such as the one depicted in FIG. 43 each engaged with a buckle and a bone to be fixated.

As depicted, for example, in FIGS. 50-51, multiple tensioners each using separate cords may be used on a larger fracture. With a tensioner (e.g. 1000) including a single arm (e.g. 1010) extending longitudinally from a housing (e.g. 1030), multiple tensioners (e.g. tensioners 2000 and 3000 in FIGS. 48-49) may be used side by side and abutting or nesting directly next to each other of each tensioner. In this example, removable handle 1050 may, for example, be removed from one tensioner 2000 to be used with another tensioner 3000 to provide individual and/or different tensions to one or multiple cords applied to the same bone fracture.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

We claim:

1. A fracture fixation system comprising:
a cord, said cord including a first end and a second end, said cord configured to extend around a bone to provide fixation to a fracture of the bone;
a connector, said connector including a body, the body including a longitudinal axis and extending from a proximal end to a distal end opposite the proximal end, the first end of said cord connectable to the distal end of the body, said connector further comprising a first lock member at the proximal end of the body and a second lock member positioned between the proximal end and the distal end, the first lock member and second lock member extending in a lateral direction relative to the longitudinal axis, the body defining a first slot between the first lock member and the second lock member and a second slot between the second lock member and a portion of the body towards the distal end, portions of said cord passable through the first and second slots and around portions of the first and second lock members to tighten the cord to provide the fixation of the fracture, the second lock member comprising an engagement portion configured to receive overlapping portions of said cord passing through the second slot, the engagement portion defining a proximal end surface of the second slot that is concave in the longitudinal direction as it extends along the lateral direction of the second lock member, wherein the distal end of the body comprising a hook, the hook including two prongs, the prongs and a portion of the body forming cord engagement spaces, the hook including a top surface and a bottom surface, wherein cord engagement channels are formed in the bottom surface of the hook and extending from the cord engagement spaces to the distal end of the body of said connector, the cord engagement spaces and cord engagement channels configured to receive portions of said cord.

2. The system of claim 1, wherein the engagement portion is arcuately concave in the longitudinal direction as it extends along the lateral direction of the second lock member.

3. The system of claim 1 wherein the engagement portion of the second lock member is convex along a thickness extending between a top surface and a bottom surface of the body.

4. The system of claim 1 wherein the body of said connector further comprising slots on opposite lateral sides of the body and aligned longitudinally relative to the longitudinal axis extending from the proximal end of the body, the slots configured to engage a tensioner.

5. The system of claim 4, wherein the tensioner engages with the slots to hold said connector to allow a user to provide tension to said cord to fixate the fracture.

6. The system of claim 4, wherein said tensioner comprises a body having a longitudinal axis, a handle connectable to the body at a first end, and an arm extending along the longitudinal axis of the body of said tensioner from a second end opposing the first end of the body, a distal end of the arm configured to engage the slots of said connector, wherein the body of the tensioner defines a passage to receive said cord, said cord extending through the passage of the body, the second end of said cord exiting the body of the tensioner and accessible to a user.

7. The system of claim 6, wherein the handle is removably connectable to the body of the tensioner.

8. The system of claim 6, wherein the handle is rotatable relative to a rotatable member housed within the body of the tensioner, wherein the handle, when removable attached to the body of the tensioner, is configured to rotate the rotatable member to twist a portion of said cord.

9. The system of claim 4 further comprising a second cord configured to extend around the bone to provide additional fixation to the fracture of the bone, a second connector and a second tensioner to provide a tension of said second cord to further fixate the fracture, said second connector including a proximal end for connecting to a first end of said second cord and a distal connecting end relative to the proximal end for attaching to a second end of said second cord, the handle of the first tensioner removable from the first tensioner and usable with the second tensioner.

10. The system of claim 1 further comprising a first bone plate, said first bone plate including a plurality of openings for receiving screws to connect said first bone plate to the bone, wherein a portion of said cord is aligned about perpendicular to a longitudinal dimension of said first bone plate.

11. The system of claim 10, wherein said cord extends through a lateral bore formed through said first plate.

12. The system of claim 10 further comprising a second bone plate, said second bone plate including a plurality of openings for receiving screws to connect said second bone plate to an opposing side of the bone to which said first bone plate is connected, wherein a portion of said cord is aligned about perpendicular to a longitudinal dimension of said first bone plate.

13. The system of claim 12, wherein said second bone plate including a first surface contacting the bone and an opposing second surface facing away for the bone, the second surface defining a channel, the channel receiving a portion of said cord extending around the bone.

14. The system of claim 13, wherein the channel defined by the second surface is formed between two projections extending outwardly from the second surface of said second bone plate.

* * * * *